US012708364B1

(12) United States Patent
Carrico et al.

(10) Patent No.: US 12,708,364 B1
(45) Date of Patent: Aug. 18, 2026

(54) TECHNOLOGIES FOR ENABLING ELECTRONIC LOCKOUT OF A SURGICAL STAPLER USING NEAR FIELD COMMUNICATION

(71) Applicant: Cilag GmbH International, Zug (CH)

(72) Inventors: Evan Carrico, Cincinnati, OH (US); Joseph E. Murphy, Cincinnati, OH (US); Daniel Dlugos, Cincinnati, OH (US); Maxime Tremblay, Cincinnati, OH (US); Phuong Lam, Cincinnati, OH (US); Sree Shankar Satheesh Babu, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/311,647

(22) Filed: Aug. 27, 2025

(51) Int. Cl.

| | |
|---|---|
| ***A61B 17/064*** | (2006.01) |
| ***A61B 17/072*** | (2006.01) |
| *A61B 17/00* | (2006.01) |

(52) U.S. Cl.
CPC .. *A61B 17/072* (2013.01); *A61B 2017/00039* (2013.01); *A61B 2017/00221* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC ........ A61B 17/072; A61B 2017/00039; A61B 2017/00221; A61B 2017/07257; A61B 2017/07271; A61B 2017/07278; A61B 2017/07285
See application file for complete search history.

(56) References Cited

U.S. PATENT DOCUMENTS

| | | | |
|---|---|---|---|
| 5,395,033 | A | 3/1995 | Byrne et al. |
| 7,644,848 | B2 | 1/2010 | Swayze et al. |
| 7,721,931 | B2 | 5/2010 | Shelton, IV et al. |
| 8,753,338 | B2 | 6/2014 | Widenhouse et al. |
| 9,265,585 | B2 | 2/2016 | Wingardner et al. |
| 9,615,888 | B2 | 4/2017 | Manzo et al. |
| 9,668,735 | B2 | 6/2017 | Beetel |
| 9,877,718 | B2 | 1/2018 | Weir et al. |

(Continued)

FOREIGN PATENT DOCUMENTS

| | | | |
|---|---|---|---|
| EP | 0679367 | A2 | 11/1995 |
| EP | 2364666 | A1 | 9/2011 |
| WO | 2012112249 | A1 | 8/2012 |

*Primary Examiner* — Eyamindae C Jallow
(74) *Attorney, Agent, or Firm* — Barnes & Thornburg LLP

(57) ABSTRACT

Technologies for enabling electronic lockout of a surgical stapler includes an electronic lockout system having a sensor controller and a near field communication (NFC) sensor circuit including a primary NFC coil. The sensor controller is configured to energize the primary NFC coil to generate a primary magnetic field, determine a present resonant frequency of the NFC sensor circuit based on the primary magnetic field and a secondary magnetic field generated by a secondary NFC coil located on a staple cartridge, compare the present resonant frequency to an expected resonant frequency, and determined, based on the comparison, whether to enable lockout of the surgical stapler to prevent firing of the surgical stapler. Additional embodiments utilize configurable circuits to effect NFC communication between the primary and secondary coils and inductance sensing of a sled of the staple cartridge.

20 Claims, 18 Drawing Sheets

(56) References Cited

U.S. PATENT DOCUMENTS

| | | | |
|---|---|---|---|
| 10,190,888 | B2 | 1/2019 | Hryb et al. |
| 10,206,678 | B2 | 2/2019 | Shelton, IV et al. |
| 10,271,844 | B2 | 4/2019 | Valentine et al. |
| 10,595,836 | B2 | 3/2020 | Smaby et al. |
| 10,828,030 | B2 | 11/2020 | Weir et al. |
| 11,559,366 | B2 | 1/2023 | Overmyer et al. |
| 11,653,915 | B2 | 5/2023 | Shelton, IV et al. |
| 11,937,816 | B2 | 3/2024 | Huang |
| 11,992,210 | B2 | 5/2024 | Shelton, IV et al. |
| 12,082,806 | B2 | 9/2024 | Giordano et al. |
| 12,268,388 | B2 | 4/2025 | Fiebig et al. |
| 12,484,900 | B2 | 12/2025 | Ryle et al. |
| 12,544,067 | B2 | 2/2026 | Batty et al. |
| 2016/0030042 | A1 | 2/2016 | Heinrich et al. |
| 2018/0042658 | A1 | 2/2018 | Shelton, IV et al. |
| 2019/0015102 | A1 | 1/2019 | Baber et al. |
| 2019/0200997 | A1 | 7/2019 | Shelton, IV et al. |
| 2022/0273306 | A1* | 9/2022 | Shelton, IV ..... A61B 17/07207 |
| 2022/0273307 | A1* | 9/2022 | Shelton, IV ............. H04B 5/70 |
| 2024/0366221 | A1 | 11/2024 | Marriott et al. |
| 2024/0415510 | A1 | 12/2024 | Schings et al. |
| 2024/0423615 | A1 | 12/2024 | Shelton, IV et al. |
| 2025/0000510 | A1 | 1/2025 | Creamer et al. |
| 2025/0017585 | A1 | 1/2025 | Nalagatla et al. |
| 2025/0025155 | A1 | 1/2025 | Batty et al. |
| 2025/0025156 | A1 | 1/2025 | Shelton, IV et al. |
| 2025/0025157 | A1 | 1/2025 | Batty et al. |
| 2025/0025158 | A1 | 1/2025 | Ryle et al. |
| 2025/0025159 | A1 | 1/2025 | Batty et al. |
| 2025/0025160 | A1 | 1/2025 | Batty et al. |
| 2025/0025162 | A1 | 1/2025 | Ahrens et al. |
| 2025/0025164 | A1 | 1/2025 | Batty et al. |
| 2025/0025165 | A1 | 1/2025 | Ryle et al. |
| 2025/0025167 | A1 | 1/2025 | Ryle et al. |
| 2025/0025168 | A1 | 1/2025 | Ryle et al. |
| 2025/0025169 | A1 | 1/2025 | Batty et al. |
| 2025/0025170 | A1 | 1/2025 | Bertram et al. |
| 2025/0120718 | A1 | 4/2025 | Shelton, IV et al. |
| 2025/0312040 | A1 | 10/2025 | Overmyer |
| 2025/0375200 | A1 | 12/2025 | Batty et al. |

* cited by examiner

TECHNOLOGIES FOR ENABLING ELECTRONIC LOCKOUT OF A SURGICAL STAPLER USING NEAR FIELD COMMUNICATION

TECHNICAL FIELD

The present disclosure relates generally to surgical instruments and, more particularly, to surgical stapling and cutting instruments and associated staple cartridges for use with the surgical instruments to facilitate the cutting and stapling of patient tissue.

BACKGROUND

Surgical procedures often involve the use of various surgical instruments to assist a surgeon in the performance of the corresponding procedure. Recently, minimally invasive surgical (MIS) instruments have gained preference over traditional "open" surgical devices as the use of MIS instruments can reduce post-operative recovery time and associated tissue scarring. Endoscopy and laparoscopy are common types of MIS procedures in which a tube or trocar is inserted into natural or surgically-made openings (e.g., incisions) of the patient, depending on the particular procedure. The tube or trocar is then used to facilitate introduction of associated surgical instruments into the patient's body (e.g., the patient's abdominal cavity) to treat internal tissue of the patient.

One type of surgical instrument usable in MIS procedures is a surgical stapler, sometimes referred to as an "endocutter." A typical surgical stapler includes an elongated shaft to facilitate use of a trocar and an end effector located at a distal end of the elongated shaft. The elongated shaft facilitates the use of the surgical stapler with a trocar to access the patient's anatomical environment (e.g., the patient's abdominal cavity) and may include one or more articulation joints to increase the usability of the surgical stapler in the anatomical environment. Similarly, the end effector may be attached to the elongated shaft via an articulation joint to allow the end effector to be positioned as desired by the surgeon. A typical end effector of a surgical stapler includes a pair of jaws movable between an open position and a closed position to facilitate the grasping of tissue within the jaws. One of the jaws is embodied as a cartridge jaw and is configured to receive a staple cartridge, and the other jaw is embodied as an anvil jaw configured to provide a surface on which the staples are formed. The end effector also includes a cutting element (typically referred to as a "knife"), which is translated distally along the end effector during a firing phase of the surgical stapler to transect tissue presently grasped by the end effector. As the knife advances along the end effector, staples contained in the staple cartridge are progressively ejected to thereby seal opposing sides of the transected tissue.

Surgical staplers may be embodied as independent, hand-held devices or configured to be coupled to a robotic surgery system. In hand-held embodiments, the surgical stapler may include a handle and an associated trigger, which is operable by a surgeon to control the end effector and the ejection of the staples from the staple cartridge. In robotic embodiments, the surgical stapler is configured to be mounted to a robotic arm of a robotic manipulator, which is controllable by the surgeon via a remote control console. For example, the control console may include various input devices that can be grasped and manipulated by the surgeon to cause movement and firing of the surgical stapler.

In some typical surgical staplers, one or more mechanical "lockouts" may be employed to prevent firing of the surgical stapler if an associated staple cartridge is missing or spent (i.e., has been previously fired). However, while mechanical lockouts provide a physical prevention of the firing of the surgical stapler, typical mechanical lockouts consume valuable space within the end effector of the surgical stapler. As such, electronic lockouts are sometimes employed in surgical staplers to preserve space.

SUMMARY

According to an aspect of the present disclosure, a surgical stapler may include an end effector, a sensor controller, and an NFC sensor circuit including a primary NFC coil. The end effector may be configured to receive the staple cartridge and may include a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller may be configured to energize the primary NFC coil to generate a primary magnetic field to induce a current in the secondary NFC coil, determine a first resonant frequency of the NFC sensor circuit based on the primary magnetic field and a secondary magnetic field generated by the secondary NFC coil, compare the first resonant frequency of the NFC sensor circuit to an expected resonant frequency of the NFC sensor circuit when the metallic sled is in the home position and interacting with the magnetic field generated by the primary NFC coil, and determine, based on the comparison of the first resonant frequency and the expected resonant frequency, whether to enable lockout of the surgical stapler to prevent firing of the surgical stapler.

In some embodiments, the end effector may include a jaw assembly having a cartridge jaw and an anvil jaw opposite the cartridge jaw. The cartridge jaw may include a floor wall and a pair of opposing sidewalls extending up from the floor wall to define a channel configured to receive the staple cartridge. A first sidewall of the pair of opposing sidewalls may include a recess defined on an internal surface facing the channel. The surgical stapler may include a circuit board, and the sensor controller and the NFC sensor circuit may be mounted on the circuit board. The circuit board may be located within the recess of the first sidewall such that the NFC primary coil of the NFC sensor circuit is laterally adjacent to the metallic sled when the metallic sled is in the home position.

Additionally, in some embodiments, the first resonant frequency of the NFC sensor circuit may be dependent on whether the metallic sled is located in the home position and interacting with the magnetic field generated by the secondary NFC sensor coil. Additionally, the primary NFC coil and the secondary NFC coil may be tuned to the expected resonant frequency with the metallic sled in the home position.

In some embodiments, the sensor controller may include an NFC reader circuit configured to energize the primary NFC coil to generate a magnetic field to induce a current in the secondary NFC coil of the staple cartridge and receive, in response to the induced current, data from a responder circuit of the staple cartridge transferred via the secondary NFC coil. Additionally, in some embodiments, the sensor controller may be further configured to respond to the lockout status request with an indication of whether the lockout of the surgical stapler is enabled or disabled based on the first resonant frequency of the inductance sensor circuit.

According to another aspect of the present disclosure, a surgical stapler may include an end effector, a sensor controller, and an NFC sensor circuit located in the end effector and including a primary NFC coil. The end effector may be configured to receive the staple cartridge. The staple cartridge may include a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller may include a mode controller and an NFC control circuit. The mode controller may be configured to selectively configure the NFC control circuit between an inductance sensing circuit and an NFC reader circuit. The primary NFC coil may form an inductance sensor coil of the inductance sensing circuit while the NFC control circuit is configured as the inductance sensing circuit. The sensor controller may be configured to use the inductance sensing circuit to determine whether the sled is in the home position and use the NFC reader circuit to read data from the staple cartridge via the secondary NFC coil.

In some embodiments, the sensor controller may be configured to determine a mode for the NFC control circuit between an inductance sensing mode and an NFC reading mode. The sensor controller may be further configured to, in response to a determination that the mode for the NFC control circuit is the inductance sensing mode, control the mode controller to configure the NFC control circuit as the inductance sensing circuit; energize, using the inductance sensing circuit, the inductance sensor coil to generate a magnetic field; determine a first resonant frequency of the inductance sensing circuit based on the magnetic field; compare the first resonant frequency of the inductance sensing circuit to an expected resonant frequency of the inductance sensing circuit; and determine, based on the comparison of the first resonant frequency and the expected resonant frequency, whether to enable lockout of the surgical stapler to prevent firing of the surgical stapler.

Additionally, in some embodiments, the inductance sensor circuit may include a tank circuit having a capacitor and the inductance sensor coil. Additionally, the first resonant frequency of the NFC sensor circuit may be dependent on whether the metallic sled is located in the home position and interacting with the magnetic field generated by the inductance sensing circuit. Furthermore, in some embodiments, the primary NFC coil and the secondary NFC coil may be tuned to the expected resonant frequency with the metallic sled in the home position. Additionally, the sensor controller may be further configured to respond to the lockout status request with an indication of whether the lockout of the surgical stapler is enabled or disabled based on the first resonant frequency of the inductance sensing circuit.

In some embodiments, the sensor controller may be configured to determine a mode for the NFC control circuit between an inductance sensing mode and an NFC reading mode. The sensor controller may be further configured to, in response to a determination that the mode for the NFC control circuit is the NFC reading mode, control the mode controller to configure the NFC control circuit as the NFC reader circuit; energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil. Additionally, in some embodiments, the mode controller may be configured to control an electronic switch to selectively couple either (i) a first capacitor in series with the primary NFC coil to form the NFC reader circuit or (ii) a second capacitor in parallel with the primary NFC coil to form the inductance sensing circuit.

According to a further aspect of the present disclosure, a surgical stapler may include an end effector, a sensor controller, and an NFC sensor circuit including a primary NFC coil and an inductance sensor coil. The end effector may be configured to receive the staple cartridge. The staple cartridge may include a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller may include a mode controller and an NFC control circuit. The mode controller may be configured to selectively configure the NFC control circuit between (i) an inductance sensing circuit by electrically coupling the inductance sensor coil to the NFC control circuit and (ii) an NFC reader circuit by electrically coupling the primary NFC coil to the NFC control circuit. The sensor controller may be configured to use the inductance sensing circuit to determine whether the sled is in the home position and use the NFC reader circuit to read data from the staple cartridge via the secondary NFC coil.

In some embodiments, the sensor controller may be configured to determine a mode for the NFC control circuit between an inductance sensing mode and an NFC reading mode. The sensor controller may be further configured to, in response to a determination that the mode for the NFC control circuit is the inductance sensing mode, control the mode controller to electrically couple the inductance sensor coil to the NFC control circuit to form the inductance sensing circuit; energize, using the inductance sensing circuit, the inductance sensor coil to generate a magnetic field; determine a first resonant frequency of the inductance sensing circuit based on the magnetic field; compare the first resonant frequency of the inductance sensing circuit to an expected resonant frequency of the inductance sensing circuit; and determine, based on the comparison of the first resonant frequency and the expected resonant frequency, whether to enable lockout of the surgical stapler to prevent firing of the surgical stapler.

Additionally, in some embodiments, the first resonant frequency of the inductance sensing circuit may be dependent on whether the metallic sled is located in the home position and interacting with the magnetic field generated by the inductance sensing coil. Additionally, the inductance sensing coil may be tuned to the expected resonant frequency with the metallic sled in the home position. Furthermore, in some embodiments, the sensor controller may be further configured to respond to the lockout status request with an indication of whether the lockout of the surgical stapler is enabled or disabled based on the first resonant frequency of the inductance sensing circuit.

In some embodiments, the sensor controller may be configured to determine a mode for the NFC control circuit between an inductance sensing mode and an NFC reading mode. The sensor controller may be further configured to, in response to a determination that the mode for the NFC control circuit is the NFC reading mode, control the mode controller to electrically couple the primary NFC coil to the NFC control circuit to form the NFC reader circuit; energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil.

BRIEF DESCRIPTION OF THE DRAWINGS

The detailed description particularly refers to the following figures, in which.

DETAILED DESCRIPTION OF THE DRAWINGS

Figure 1:
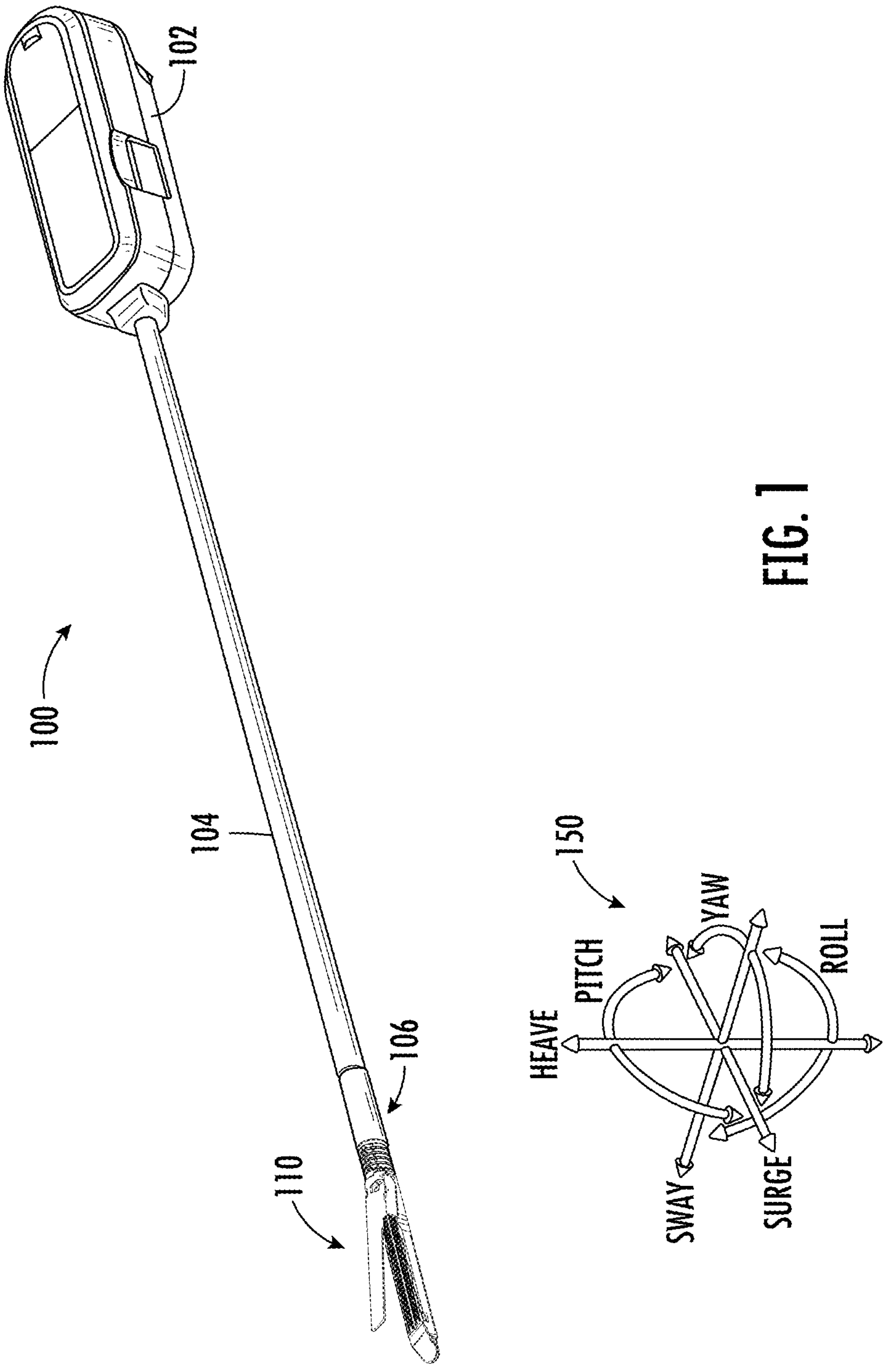
FIG. 1 is a perspective view of an embodiment of a surgical stapler configured for use with a robotic surgical system.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, et cetera, may be used throughout the specification in reference to the surgical instruments described herein as well as in reference to the patient's natural anatomy. Such terms have well-understood meanings in both the study of anatomy and the field of surgery. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

Portions of the disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a surgical stapler or "endocutter" 100 is configured for use in minimally invasive surgery (MIS) procedures including, but not limited to, endoscopic and laparoscopic procedures. The surgical stapler 100 is configured to contemporaneously transect and staple tissue during the performance of such surgical procedures. Although the concepts presented below are described in regard to a surgical stapler, it should be appreciated that the presented concepts may be applicable to other types of surgical instruments configured to perform different surgical functions including, but not limited to, surgical scissors, tissue graspers, energy-based surgical instruments, clip appliers, needle drivers, and/or other surgical instruments.

The illustrative surgical stapler 100 includes a drive housing 102, an elongated shaft 104 that extends distally away from the drive housing 102, and an end effector 110 located at a distal end of the elongated shaft 104 opposite the drive housing 102. As discussed in more detail below, the surgical stapler 100 is embodied as a robotic surgical stapler and is configured to be used with a corresponding robotic surgical system. As such, the drive housing 102 includes coupling features that that facilitate the mounting of the drive housing 102 to a robotic arm of a robotic manipulator of the robotic surgery system as discussed below in regard to FIGS. 8 and 9. The mounting of the drive housing 102 to the robotic arm allows the robotic manipulator to control various functions of the surgical stapler 100, including the movement and "firing" of the end effector 110, as discussed in more detail below.

The elongated shaft 104 is sized and configured for use in minimally invasive surgery procedures. For example, the elongated shaft 104 has a length and diameter that is sized to allow the elongated shaft 104 to be inserted into a trocar or similar surgical tube to allow positioning of the end effector 110 into the patient's anatomical environment (e.g., the patient's abdominal cavity). Illustratively, the distal end of the elongated shaft 104 is coupled to the end effector 110 via an articulable joint 106, which allows the end effector 110 to be moved to different orientations and/or positions relative to the elongated shaft 104.

In the illustrative embodiment, the articulable joint 106 provides six degrees of freedom to the end effector 110. For example, as indicated by coordinate frame 150, the degrees of freedom of the end effector 110 may include three translational degrees (i.e., surge, heave, and sway) and three rotational degrees (i.e., roll, pitch, and yaw). The "surge" degree of freedom refers to forward and backward translational movement of the end effector 110 relative to the elongated shaft 104, the "heave" degree of freedom refers to upward and downward translational movement of the end effector 110 relative to the elongated shaft 104, and the "sway" degree of freedom refers to left and right translational movement of the end effector 110 relative to the elongated shaft 104. The "roll" degree of freedom refers to rotation of the end effector 110 along a longitudinal axis defined by the end effector 110, the "pitch" degree of freedom refers to upward and downward tilting of the end effector 110 relative to the elongated shaft 104, and the "yaw" degree of freedom refers to leftward or rightward turning of the distal end of the end effector 110 relative to the elongated shaft 104.

The elongated shaft 104 also houses a portion of an actuation system (not shown) to control the movement and activation (e.g., the "firing") of the end effector 110. The actuation system may include various articulation cables, push rods, firing rods, and/or other devices, which extend through the elongated shaft 104 from mechanisms located in the drive housing 102 to components of the articulable joint 106 and/or the end effector 110. In this way, the drive housing 102 is configured to control the movement and activation (i.e., the "firing") of the end effector 110.

Figure 2:
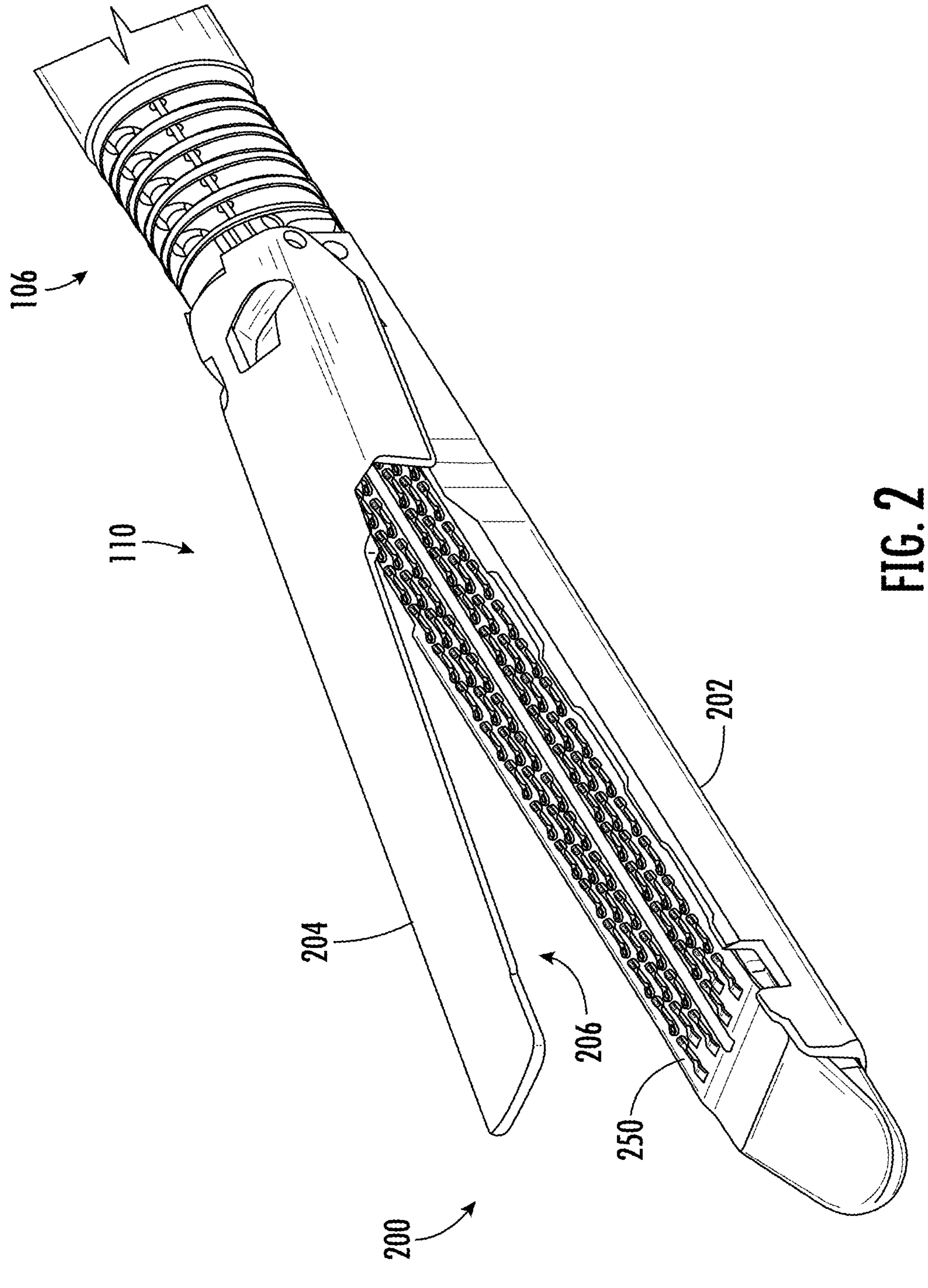
FIG. 2 is a perspective view of an embodiment of an end effector of the surgical stapler of FIG. 1.

Referring now to FIG. 2, the end effector 110 includes a jaw assembly 200, which illustratively includes a pair of jaws 202, 204 that oppose each other. The jaw 202 is illustratively embodied as a "cartridge" jaw and includes a channel 300 (see FIG. 3) configured to receive a staple cartridge 250. The jaw 204 is illustratively embodied as an "anvil" jaw and includes a bottom surface 206 having forming pockets configured to deform staples ejected from the staple cartridge 250.

The jaw assembly 200 is movable between an open state in which the anvil jaw 204 is positioned away from the cartridge jaw 202 and a closed state in which the anvil jaw 204 is positioned near or otherwise contacts the cartridge jaw 202. Illustratively, the anvil jaw 204 is configured to move toward and away from the cartridge jaw 202. However, in other embodiments, the cartridge jaw 202 may be configured to move relative to the anvil jaw 204 or both jaws 202, 204 may be configured to move toward or away from each other. Additionally, it should be appreciated that the open state may correspond to a degree of openness that is less than a fully opened position of the jaw assembly 200 and the closed state may correspond to a degree of closeness that is less than a fully closed position. That is, the closed state may, for example correspond to a minimal distance between the distal ends of the cartridge jaw 202 and the anvil jaw 204 and the open state may correspond to a maximum distance between the distal ends of the jaws 202, 204. However, in other embodiments, the open state may correspond to a fully opened position of the jaw assembly 200 and the closed state may correspond to a fully closed position of the jaw assembly 200.

Figure 3:
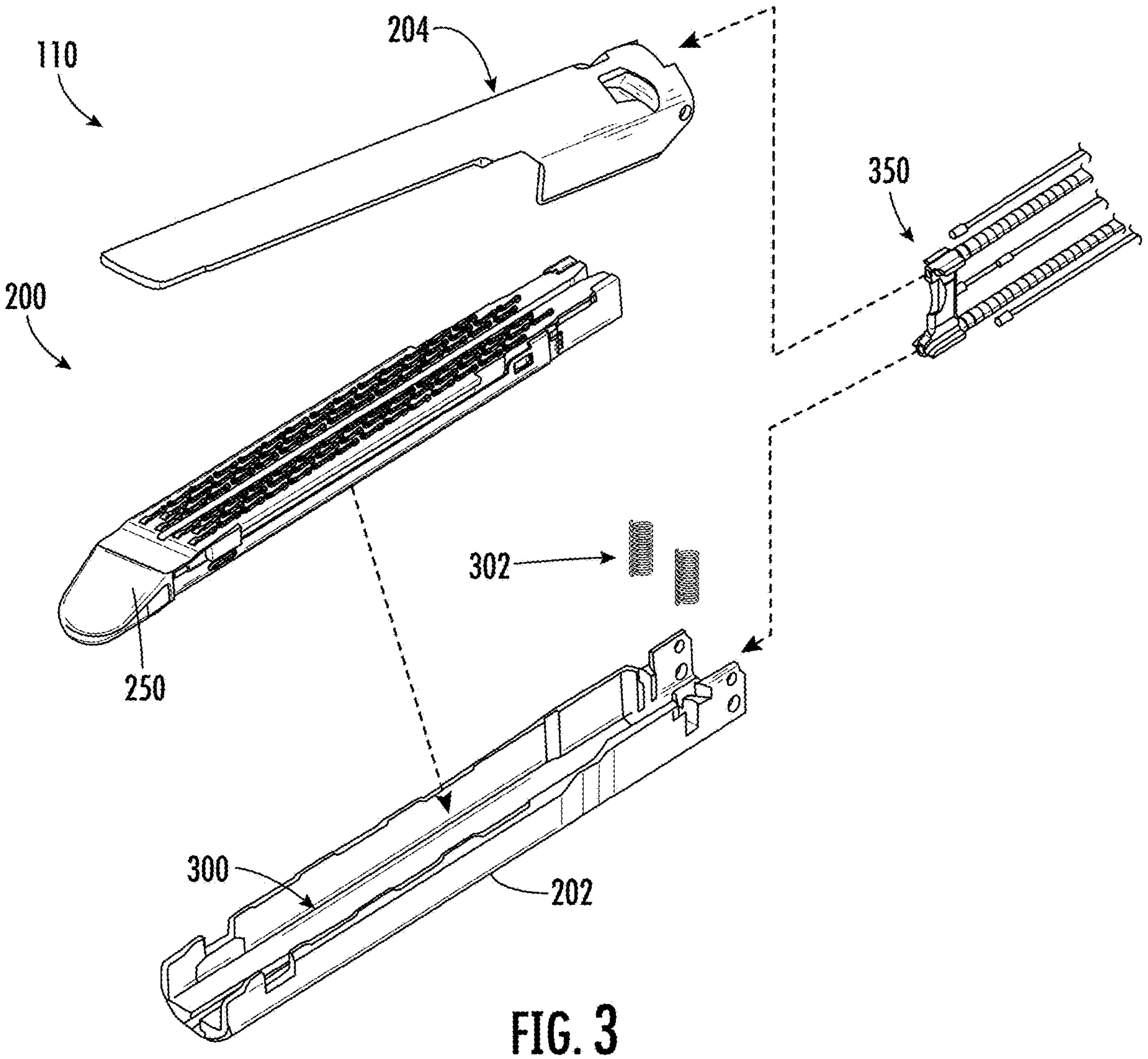
FIG. 3 is an exploded perspective view of and embodiment of a distal end of the surgical stapler of FIG. 1, including the end effector of FIG. 2.

As shown in FIG. 3, the jaw assembly 200 is biased in the open state by a pair of springs 302. That is, the springs 302 bias the anvil jaw 204 away from the cartridge jaw 202. However, actuation of the jaw assembly 200 overcomes the biasing force of the springs 302 to move the jaw assembly 200 from the open state to the closed state. When in the closed state, the end effector 110 can be "fired" to effect the cutting and stapling of tissue held within the jaw assembly 200.

The end effector 110 also includes an I-beam 350, which is configured to translate forward during the firing of the end effector 110 from the proximal end of the jaws 202 toward the distal end of the jaws 202, 204. To do so, portions of the I-beam 350 are received in corresponding channels of the cartridge jaw 202 and the anvil jaw 204 as discussed in more detail below in regard to FIGS. 4 and 5. When the end effector 110 is fired, the I-beam 350 translates forward within the channels of the jaws 202, 204. The forward movement of the I-beam 350 may cause the anvil jaw 204 to move further downward toward or against the cartridge jaw 202 and clamp the jaw assembly in the closed state.

Figure 5:
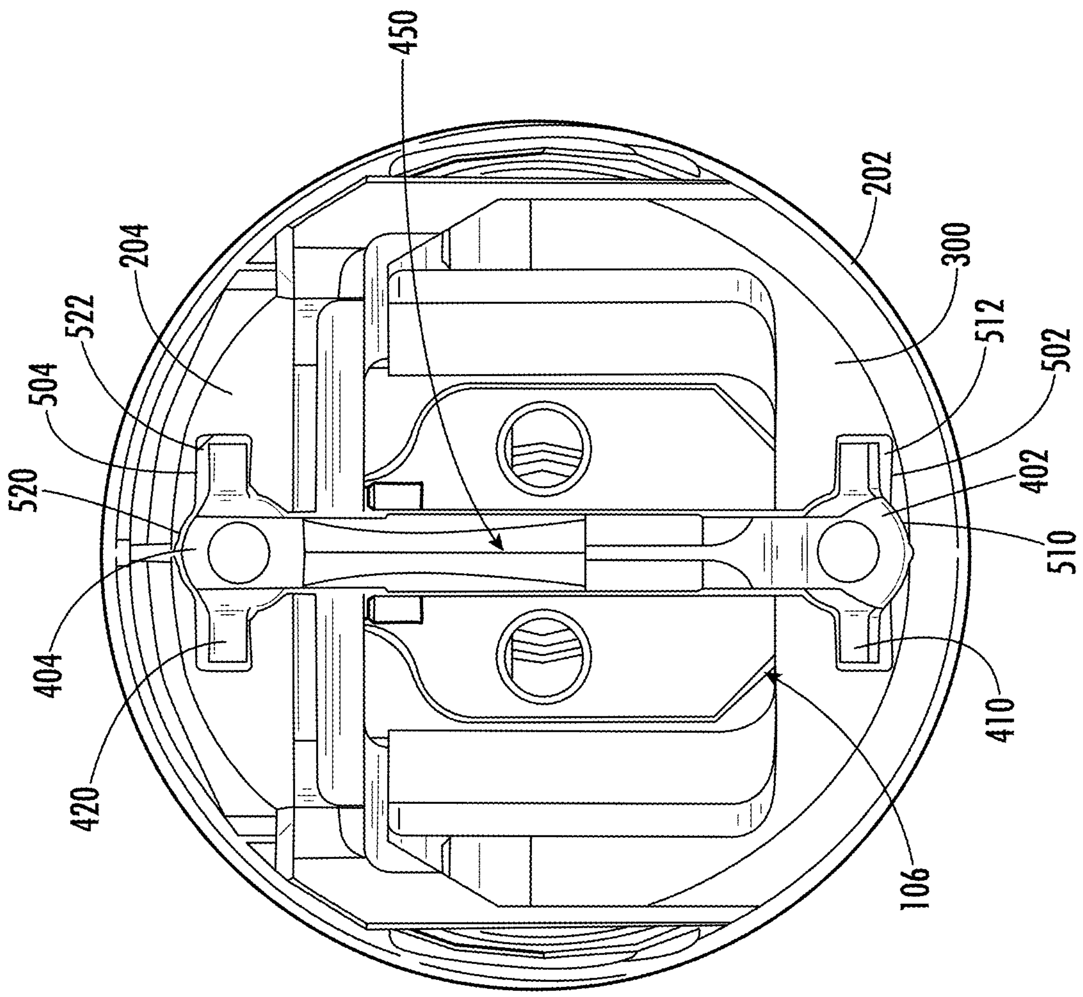
FIG. 5 is a cross-sectional view of the end effector of FIG. 1 in a closed state and showing the I-beam, of FIG. 4 received in corresponding channels of the end effector of FIG. 2 with the knife of the I-beam extending between the corresponding channels.
Figure 4:
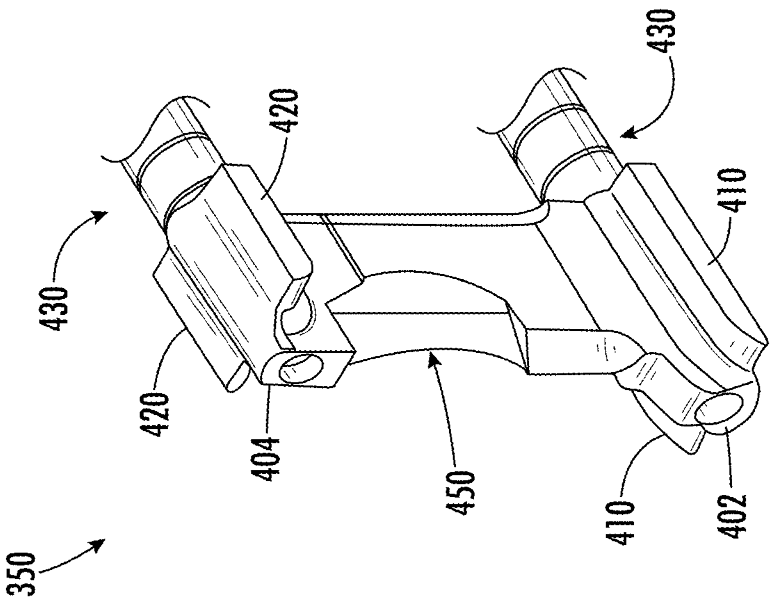
FIG. 4 is a perspective view of an embodiment of an I-beam of the end effector of FIG. 2, which includes a knife.

Referring now to FIGS. 4 and 5, the I-beam 350 includes a lower base 402, an upper base 404, and a knife 450 located between the upper and lower bases 402, 404. A pair of lower wings 410 extend laterally outward from the lower base 402. Similarly, a pair of upper wings 420 extend laterally outward from the upper base 404. A push rod 430 is coupled to each of the bases 402, 404 and to control mechanisms located in the drive housing 102. The control mechanisms of the drive housing 102 control movement of the push rods 430, which moves the I-beam 350 forward and backward within the jaw assembly 200.

When the end effector 110 is fired, the I-beam 350 moves within a lower I-beam channel 502 of the cartridge jaw 202 and an upper I-beam channel 504 of the anvil jaw 204 as shown in FIG. 5. The I-beam channel 502 of the cartridge jaw 202 includes a base channel 510 and a pair of wing channels 512, which are open to and in fluid communication with the base channel 510 and extend laterally outward therefrom. The lower base 402 of the I-beam 350 is received in and moves within the base channel 510 of the I-beam channel 502. Similarly, each lower wing 410 is received in and moves within a corresponding one of the wing channels 512. The I-beam channel 504 of the anvil jaw 204 also includes a base channel 520 and a pair of wing channels 522, which are open to and in fluid communication with the base channel 520 and extend laterally outward therefrom. The upper base 404 of the I-beam d 350 is received in and moves within the base channel 520 of the I-beam channel 502. Similarly, each upper wing 420 is received in and moves within a corresponding one of the wing channels 522.

Figure 6:
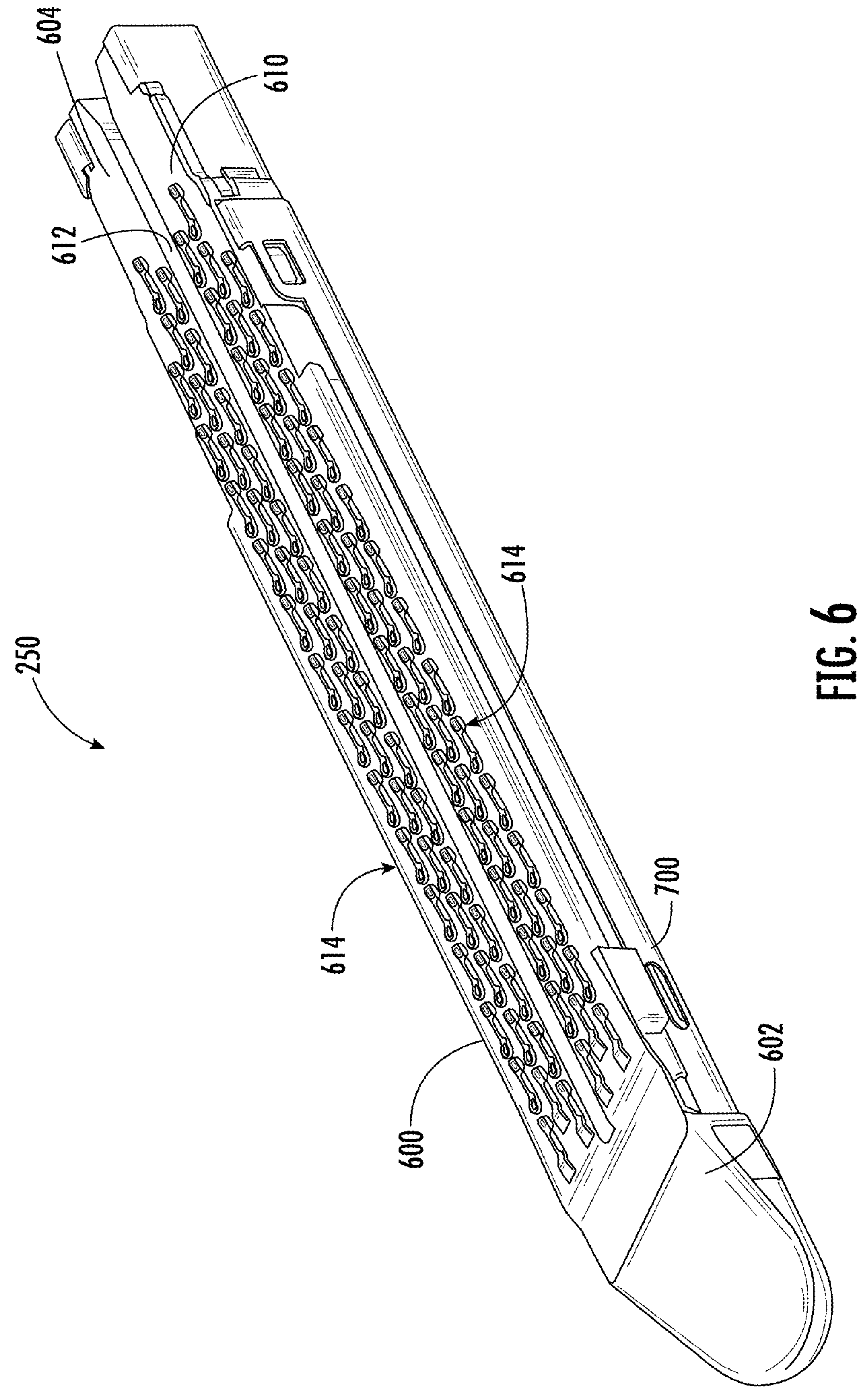
FIG. 6 is a perspective view of an embodiment of a staple cartridge that may be inserted into the end effector of FIG. 2.
Figure 7:
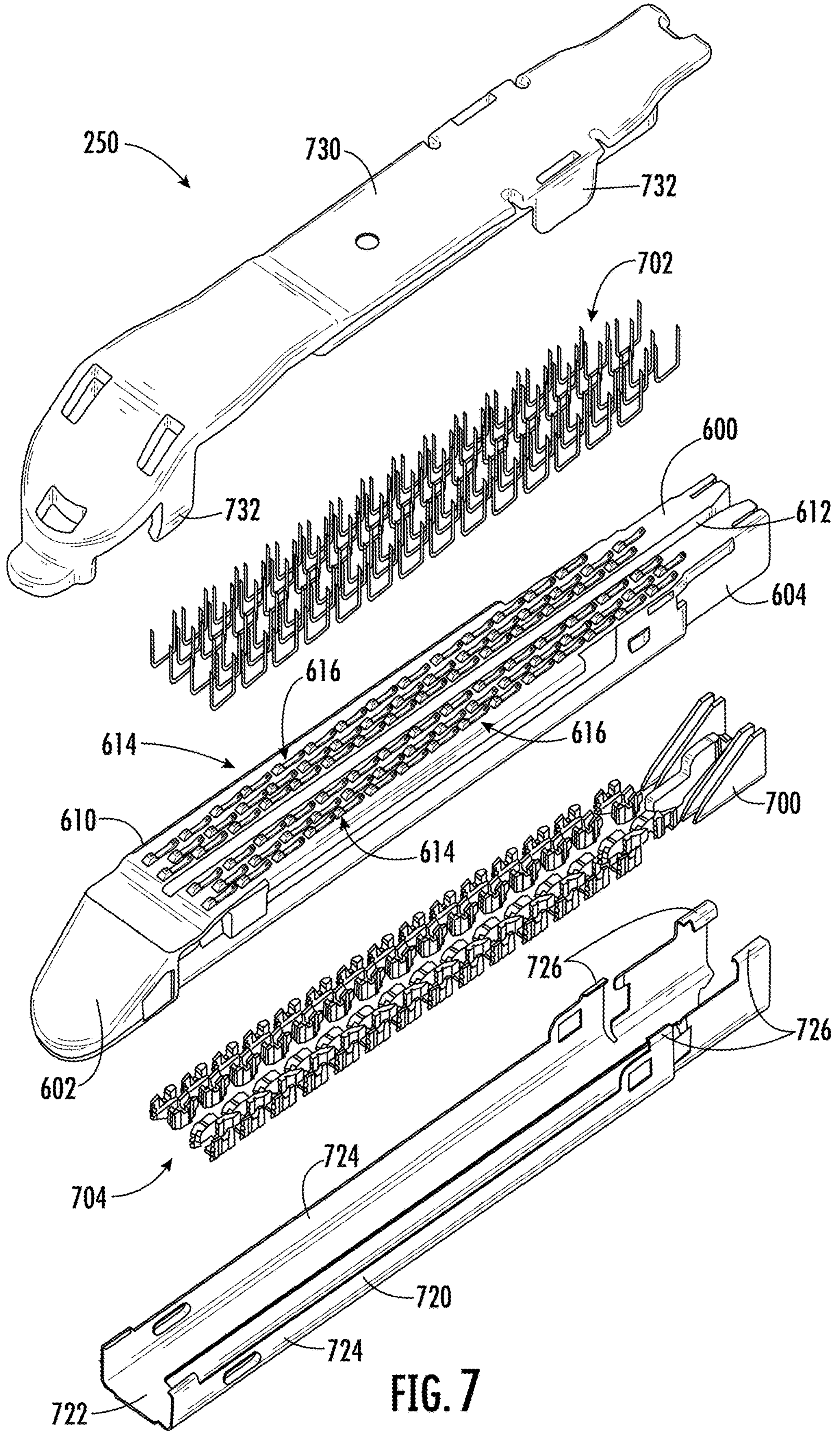
FIG. 7 is an exploded, perspective view of the staple cartridge of FIG. 6.

Referring now to FIGS. 6 and 7, the illustrative staple cartridge 250 includes a cartridge body 600 having a distal end 602 and a proximal end 604. The cartridge body 600 also includes a deck 610 that extends from the proximal end 604 to the distal end 602. The deck 610 includes a longitudinal knife slot 612 that is located centrally on the deck 610 and extends from the distal end 602 toward the proximal end 604 of the cartridge body 600. During a firing stroke of the surgical stapler 100 (i.e., when the end effector is "fired"), the I-beam 350 transversed along the longitudinal knife slot 612 with the knife 450 of the I-beam 350 protruding upwardly from the longitudinal knife slot 612 to facilitate the transection of tissue captured within in the end effector 110 and held between the staple cartridge 250 and the anvil jaw 204.

A set of staple cavities 614 are defined in the deck 610 on either side of the longitudinal knife slot 612. A staple 702 is positioned in each of the staple cavities 614 and is supported by a corresponding staple driver 704. The staple cartridge 250 also includes a staple sled 700, which is initially located toward the proximal end 604 of the cartridge body 600 and is pushed toward the distal end 602 by the I-beam 350 when the end effector 110 is fired. The staple sled 700 lifts each staple driver 704 when the sled 700 comes into contact with the corresponding staple driver 704, which ejects the staple 702 associated with the corresponding staple driver 704 from the corresponding staple cavity 614. In the illustrative embodiment, the deck 610 includes staple guides or projections 616 that project upwardly from the deck 610 around each staple cavity 614. The staple guides 616 are configured to guide or control the legs of the staples 702 as the staples 702 are being ejected from the staple cavities 614. Illustratively, the staple guides 616 are located around the distal and proximal ends of each staple cavity 614, but may completely surround each staple cavity 614 or be located on only one end of each staple cavity 614 in other embodiments. The staple guides 616 may also form a set of "teeth" and be configured to grasp tissue held within the jaw assembly 200 to restrict movement of the tissue. In other embodiments, the deck 610 of the cartridge body 600 maybe devoid of any staple guides 616.

The staple cartridge 250 also includes a pan 720, which is attached to the cartridge body 600 and is configured to retain the staple drivers 704 and associated staples 702 within the cartridge body 600. Illustratively, the pan 720 is formed from a metallic material and includes a floor 722 and a pair of sidewalls 724 that extend upwardly from the floor 722 and wrap onto the sides of the cartridge body 600. The pan 720 includes a set of attachment tabs 726 that are configured to secure the pan 720 to the cartridge body 600.

Prior to use, the staple cartridge 250 includes a cover 730 attached to the cartridge body 600. The cover 730 is configured to cover the deck 610 of the staple cartridge 250 and includes a set of attachment tabs 732 configured to secure the cover 730 to the cartridge body 600. To prepare the staple cartridge 250 for use in the end effector 110, the cover 730 is removed from the cartridge body 600.

Although not illustrated in FIGS. 6 and 7, the staple cartridge 250 may also include one or more electronic circuits or devices configured to perform one or more associated functions. For example, such electronic circuitry may include processors, digital storage devices, communication circuitry, sensor circuitry, and/or other electrical components.

Figure 8:
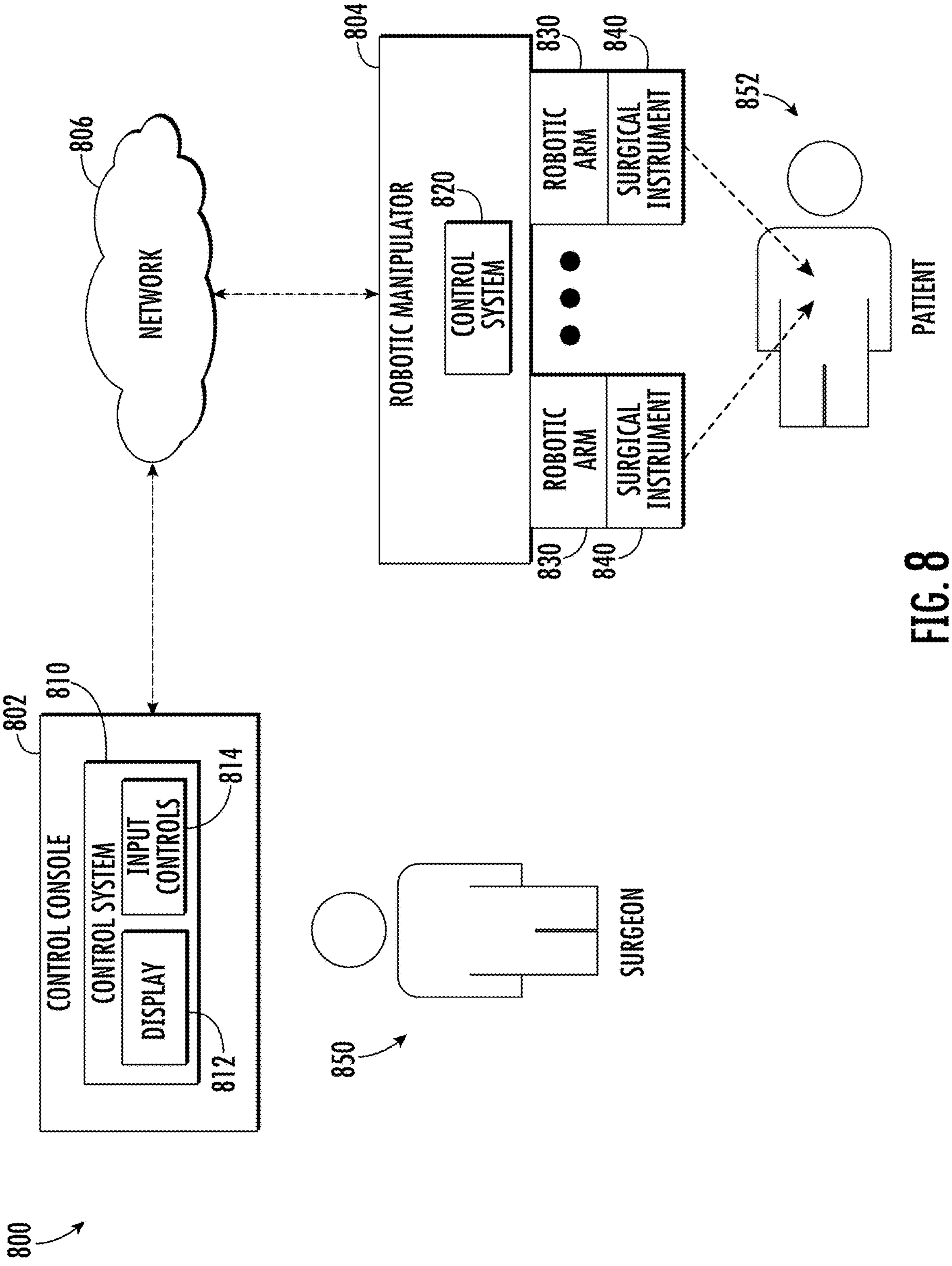
FIG. 8 is a simplified block diagram of an embodiment of a robotic surgical system including a control console and a robotic manipulator, with which the surgical stapler of FIG. 1 may be used.

Referring now to FIG. 8, as discussed above, the illustrative surgical stapler 100 is configured for use with a corresponding robotic surgical system 800. The robotic surgical system 800 includes a control console 802 and a robotic manipulator 804, which communicate with each other over a communication network 806. Although only a single control console 802 and a single robotic manipulator 804 is shown in FIG. 8, it should be appreciated that the robotic surgical system 800 may include additional control consoles 802 and/or robotic manipulators 804 in other embodiments.

The control console 802 is usable by a surgeon 850 to control the operation of the robotic manipulator 804. To do so, the control console 802 includes a control system 810. Illustratively, the control system 810 includes a display 812 and one or more input controls 814. However, it should be appreciated that the control system 810 may include additional electrical components and devices, such as a processor, a memory, and a communication subsystem to enable communications of the components of the control system 810, which are not illustrated in FIG. 8 for clarity.

The display 812 may be embodied as any type of display device capable of generating images viewable by the surgeon 850. In use, the display 812 may display images related to the surgical procedure being performed via the robotic manipulator 804. The displayed images may be obtained from, for example, an endoscopic camera operated by the robotic manipulator 804. Additionally, the display 812 may display information, including data determined by the control console 802 and/or the robotic manipulator 804, related to the surgical procedure (e.g., positional data of the robotic manipulator 804).

The input controls 814 are usable by the surgeon 850 to control the functionality of the robotic manipulator 804. The input controls 814 may be embodied as any type of input device capable of receiving a corresponding input from the surgeon 850. For example, the input controls 814 may include physical controllers, such as joy sticks, hand-held actuator modules, exoskeletal gloves, and/or other input devices. The input controls 814 may also include input devices other than hand-controlled devices such as foot pedals, vision tracking modules, and/or the like. In many embodiments, the input controls 814 are movable in multiple degrees of freedom to control the positioning and operation of the robotic manipulator 804.

The robotic manipulator 804 also includes a control system 820 and one or more robotic arms 830 to which surgical instruments 840 (e.g., the surgical stapler 100) may be mounted. In some embodiments, the robotic manipulator 804 may be mounted to a transport cart, sometimes referred to as an "arm cart," that enables mobility of the robotic manipulator 804 and the associated robotic arms 830.

The robotic arms 830 may include various articulable linkages and associated motors, which are controllable by the control console 802 to move the corresponding robotic arm 830 and any associated surgical instrument 840 to a desired position. For example, by manipulating an input control 814 of the control console 802, the surgeon 850 may control the positioning of a corresponding robotic arm 830, as well as the functionality of the associated surgical instrument 840 (e.g., the firing of the surgical stapler 100).

The control system 820 may be embodied as any type of controller or control circuit capable of controlling the functionality of the robotic manipulator including, for example, the movement of the robotic arms 830 and the activation of the surgical instruments 840 based on control signals received from the control console 802. To do so, the control system 820 may include various electrical components, circuits, and/or devices, such as a processor, a memory, and a communication subsystem to enable communications of the components of the control system 820, which are not illustrated in FIG. 8 for clarity.

In use, the robotic manipulator 804 is positioned in close proximity to a patient 852 requiring surgery. The robotic manipulator 804 may be locked or mounted in place for the duration of the surgery. The surgeon 850 may then manipulate the input controls 814 to position one or more robotic arms 830 and associated surgical instruments 840 into a desired position. For example, the surgeon 850 may position a robotic arm 830 such that an associated surgical instrument 840 is inserted through a trocar or similar elongated passageway into the anatomical environment (e.g., the abdominal cavity of the patient 852). Once so positioned, some surgical instruments 840 (e.g., an endoscope) may be locked into position to avoid unintended repositioning.

The network 806 may be embodied as any type of wired and/or wireless network or set of communication links capable of facilitating communications between the control console 802 and the robotic manipulator 804. To do so, the network 806 enable such communications using any suitable data communication specification and/or protocol. As such, in some embodiments, the network 806 may include additional devices, such as additional computers, routers, stations, and/or switches, to facilitate such communications between the control console 802 and the robotic manipulator 804.

Figure 9:
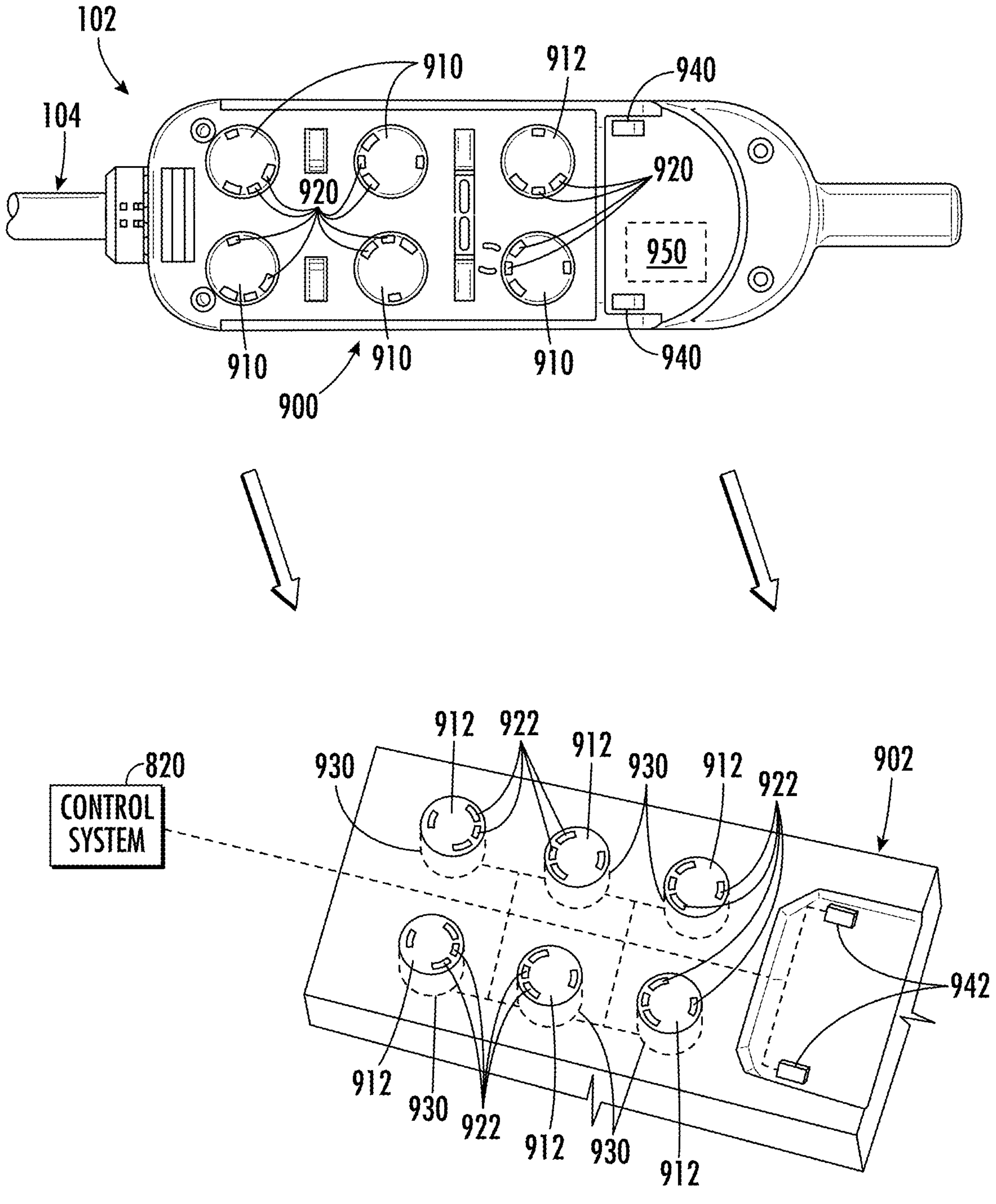
FIG. 9 is a diagrammatic view of an embodiment of a tool interface located on a bottom side of a drive housing of the surgical stapler of FIG. 1 being coupled to an arm interface located on a robotic arm of the robotic manipulator of the robotic surgical system of FIG. 8.

Referring now to FIG. 9, as discussed above, the surgical stapler 100 (and other surgical instruments 840) is configured to be mounted to a robotic arm 830 of the robotic manipulator 804. To facilitate such mounting, the drive housing 102 of the surgical stapler 100 includes a tool interface 900 located on a bottom side of the drive housing 102. The tool interface 900 is configured to mate with an arm interface 902 of the corresponding robotic arm 830 to couple the surgical stapler 100 to the robotic arm 830. The coupling of the surgical stapler 100 to the robotic arm 830 may be further facilitated via various mechanical, magnetic, and/or electrical features. In some embodiments, a sterile barrier may also be used between the surgical stapler 100 and the robotic arm 830. It should be appreciated that mounting the surgical stapler 100 to the robotic arm places the surgical stapler 100 into communication and under the control of the control system 820 of the robotic manipulator 804, which is controlled by the control console 802 as discussed above.

The tool interface 900 includes a set of input pucks 910, which are manipulable to control functions of the surgical stapler 100 such as the positioning and firing of the end effector 110. Each input puck 910 is configured to mate with a corresponding puck driver 912 of the arm interface 902. To do so, each input puck 910 includes mating features 920 that are configured to mate with mating features 922 of the corresponding puck driver 912. In the illustrative embodiment, the mating features 920 of the input pucks 910 are embodied as tabs or protrusions that extend upwardly from the corresponding input puck 910, and the mating features 922 of the puck drivers 912 are embodied as recesses configured to receive the tabs/protrusions 920 of the input pucks 910. In other embodiments, however, the mating features 920 of the input pucks 910 may be embodied as recesses and the mating features 922 of the puck drivers 912 may be embodied as tabs/protrusions.

The arm interface 902 includes an electric motor 930 operatively coupled to each puck driver 912. Each electric motor 930 is communicatively coupled to and controlled by the control system 820. Actuation of a given electric motor 930 causes actuation of the associated puck driver 912, which causes actuation of the corresponding input puck 910. For example, rotation of an electric motor 930 causes rotation of the associated puck driver 912, which causes rotation of the corresponding input puck 910. In this way, the positioning and activation (e.g., "firing") of the end effector 110 of the surgical stapler 100 may be controlled via actuation of the puck drivers 912 and associated input pucks 910.

The tool interface 900 also includes a set of electrical connectors 940, which are configured to mate with corresponding electrical connectors 942 of the arm interface 902. The electrical connectors 940, 942 provide electrical communication between the surgical stapler 100 and the robotic manipulator 804. However, in other embodiments, the surgical stapler 100 and the robotic manipulator 804 may be configured to communicate in other ways, such as via wireless communications. In some embodiments, the tool interface 900 may also include a control system 950. In such embodiments, the control system 950 may be configured to control and/or monitor various operations the surgical stapler 100. The control system 950 may include various electrical components, circuits, and/or devices, such as a processor, a memory, and a communication subsystem to enable communications of the components of the control system 950, which are not illustrated in FIG. 9 for clarity.

Figure 10:
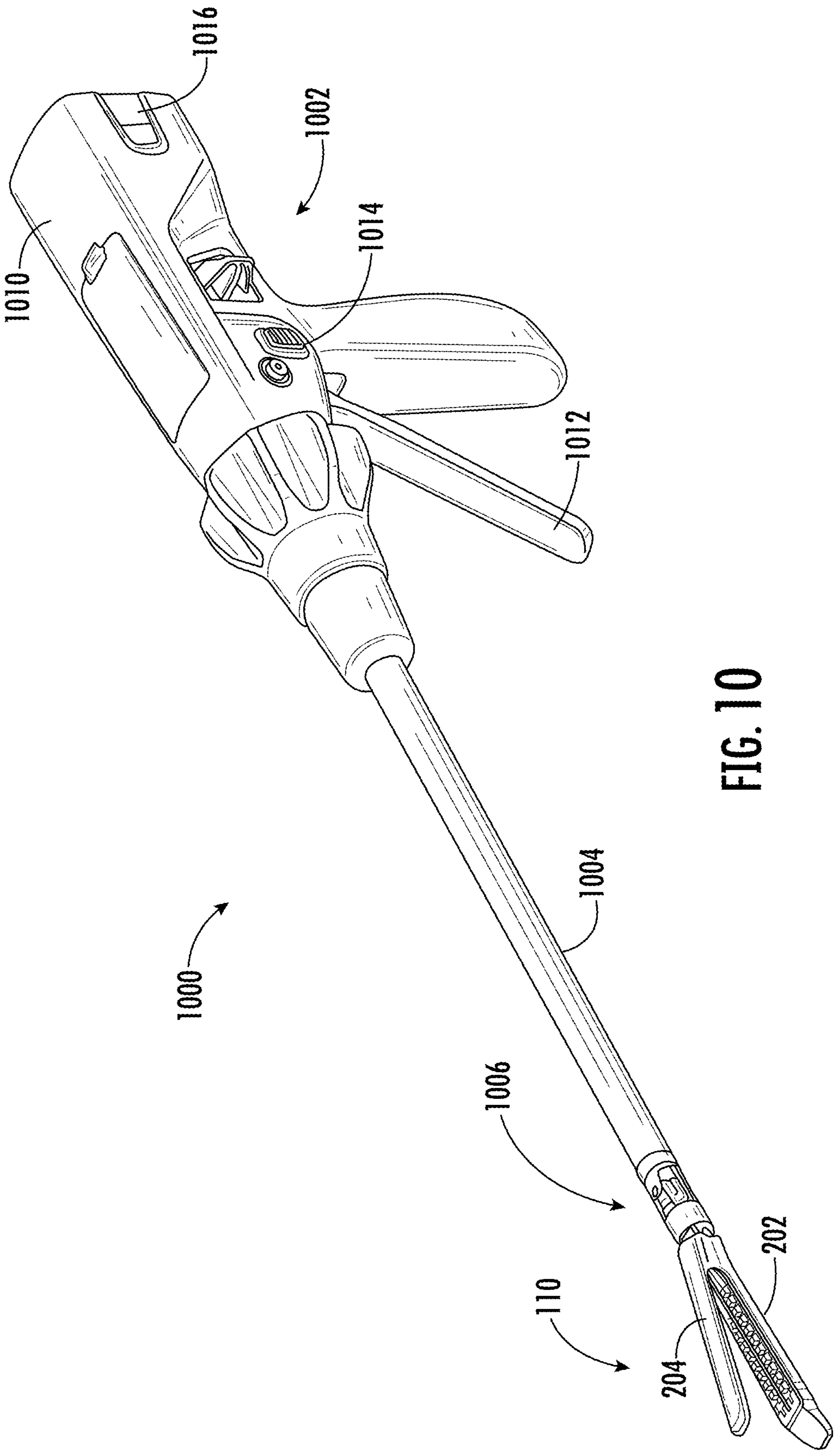
FIG. 10 is a perspective view of an embodiment of a hand-held surgical stapler including the end effector of FIG. 2.

Although the illustrative surgical stapler 100 shown and described above in regard to FIGS. 1-9 is configured for use in a robotic surgical system, the features and concepts of the surgical stapler 100 described above and below may be applicable to hand-held surgical staplers and devices. For example, as shown in FIG. 10, the end effector 110 may be incorporated into a hand-held surgical stapler 1000. The surgical stapler 1000 includes a handle 1002 and an elongated shaft 1004 extending from the handle 1002. The distal end of the elongated shaft 1004 is coupled to the end effector 110 via an articulable joint 1006, which may be substantially similar to the articulable joint 106 described above.

The handle 1002 includes a handle housing 1010 and a trigger assembly 1012 movable connected to the handle housing 1010. The trigger assembly is operable by a surgeon to move the jaw assembly 200 of the end effector 110 from the open state to the closed state as discussed above. The handle 1002 also includes one or more activation triggers 1014 to, for example, initiate the firing of the end effector 110 when in the closed state. A replaceable and/or rechargeable battery pack 1016 is coupled to an end of the handle housing 1010 and provide power to the electrical components located within the handle housing 1010.

Figure 11:
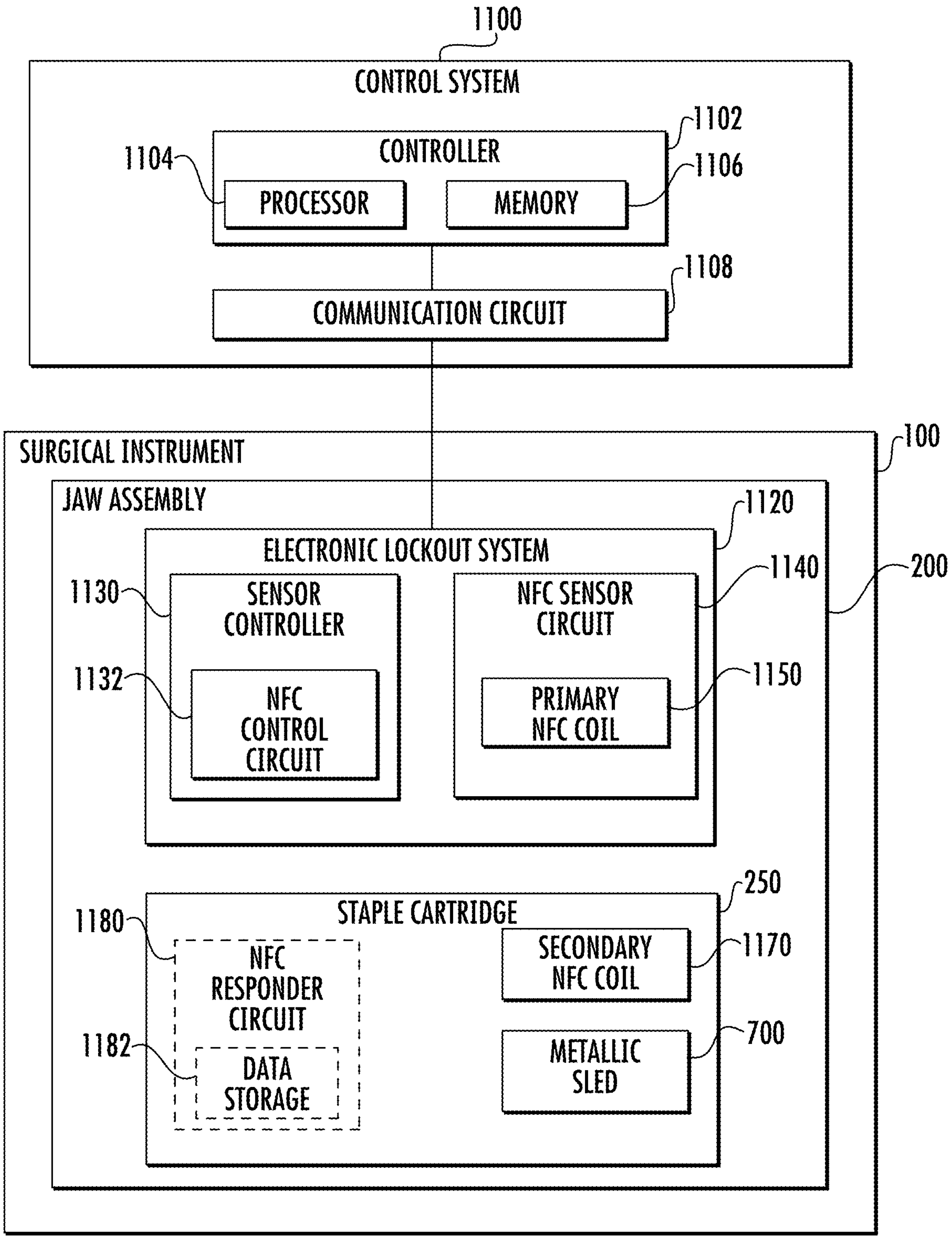
FIG. 11 is a simplified block diagram of another embodiment of a surgical system, similar to the robotic surgical system of FIG. 8, and which includes an electronic lockout system incorporated into the surgical instrument.

Referring now to FIG. 11, in some embodiments, the control system 810 of the control console 802 and/or the control system 820 of the robotic manipulator 804 is configured to enable electronic lockout of the surgical stapler 100 when the surgical stapler 100 is operatively coupled to a robotic arm 830 of the robotic manipulator 804 using mutual capacitance. In such embodiments, the control system 810, 820 is embodied as a control system 1100 configured to communicate with an electronic lockout system 1120 included in the surgical stapler 100 to control electronic lockout of the firing of the surgical stapler 100 based on the location the sled 700 in the stapler cartridge 250 (e.g., whether the sled 700 is in a home or "unspent" position or a "spent" position).

As shown in FIG. 11, the electronic lockout system 1120 includes a sensor controller 1130 and a near field communication (NFC) sensor circuit 1140. The NFC sensor circuit 1140 includes a primary NFC coil 1150, which is configured to inductively couple with a secondary NFC coil 1170 located on the staple cartridge 250 to detect when the sled 700 is in the home position as well as to receive, in some embodiments, data from a responder circuit 1180 also located on the staple cartridge as discussed in more detail below. The electronic lockout system 1120 is positioned within the jaw assembly 200 such that the primary NFC coil 1150 is aligned (e.g., laterally aligned) with the secondary NFC coil 1170 and the metallic sled 700 (or a portion of the sled 700) when the metallic sled 700 is in its home position within the staple cartridge 250.

In use, as described in more detail below, the sensor controller 1130 is configured to utilize the primary NFC coil 1150 to determine whether the sled 700 is in the home position based on a resulting resonant frequency of the NFC sensor circuit 1140. To do so, the sensor controller 1130 includes an NFC control circuit configured to energize the primary NFC coil 1150 to generate a primary magnetic field. The primary magnetic field induces a current in the secondary NFC coil 1170 through mutual inductance, which results in the secondary NFC coil 1170 generating a secondary magnetic field that interacts with the primary magnetic field to, for example, transfer data. The primary and secondary NFC coils 1150, 1170 are tuned to a resonant frequency (e.g., 13.56 megahertz) while accounting for, or otherwise relying on, the metallic sled 700 being in the home position. It should be appreciated that, when the metallic sled 700 is in the home position, the metallic sled 700 interacts with the secondary magnetic field generated by the secondary NFC coil 1170. More specifically, the secondary magnetic field creates eddy currents in the metallic sled 700, and the eddy currents create their own magnetic field about the sled 700 that interacts with (e.g., opposes) the secondary magnetic field generated by the secondary NFC coil 1170 (and, maybe, the primary NFC coil 1150), which modifies the impedance of the primary coil 1150 and which can be detected by the sensor controller 1130). It should be appreciated that the generated eddy currents can be used to "optimize" coupling and/or mutual inductance between the primary and second coils 1150, 1170. As such, the primary and secondary NFC coils 1150, 1170 are tuned or detuned to a reference resonant frequency based on the "modified" secondary magnetic field, which is altered by the presence of the sled 700 at the home position.

The sensor controller 1130 is configured to determine whether the sled 700 is in its home position based on a comparison of the present resonant frequency of the NFC sensor circuit 1140 and the tuned resonant frequency of the NFC coils 1150, 1170. However, it should be appreciated that, in other embodiments, the primary and secondary NFC coils 1150, 1170 may be tuned to a reference resonant frequency with the metallic sled 700 not in the home position and interacting with the secondary magnetic field generated by the secondary NFC coil 1170. In such embodiments, the present resonant frequency is compared to the reference resonant frequency to determine whether the sled 700 is in its home position. In either case, if the sensor controller 1130 determines that the sled 700 is not in its home position, the sensor controller 1130 reports to or otherwise instructs the control system 1100 to prevent the firing of the surgical stapler 100 and, in this way, establish an electronic lockout of the surgical stapler 100.

Similar to the control systems 810, 820, the control system 1110 may be embodied as any type of control system capable of controlling operation of the control console 802, the robotic manipulator 804, and/or the surgical stapler 100 and performing the functions described above and further below. To do so, the control system 1100 may include any suitable component, device, and/or circuit. In the illustrative embodiment, the control system 1100 includes a controller 1102 and a communication circuit 1108. It should be appreciated, however, that the control system 1100 may include other or additional components such as those commonly found in an embedded computer or computer system.

The controller 1102 may be embodied as any type of device or collection of devices capable of performing various compute and/or control functions, as described below. In some embodiments, the controller 1102 may be embodied as a single device such as an integrated circuit, an embedded system, a field-programmable-array (FPGA), a system-on-a-chip (SOC), or other integrated system or device. Additionally, in the illustrative embodiment, the controller 1102 includes or is embodied as a processor 1104 and memory 1106. The processor 1104 may be embodied as any type of processor capable of performing the functions described herein. For example, the processor 1104 may be embodied as a single or multi-core processor(s), digital signal processor, microcontroller, or other processor or processing/controlling circuit. Similarly, the memory 1106 may be embodied as any type of volatile and/or non-volatile memory and/or data storage capable of storing data generated by or otherwise obtained by the control system 1100. In operation, for example, the memory 1106 may store various data and software used during operation of the control system 1100 such as operating systems, applications, programs, libraries, and drivers.

The communication circuit 1108 of the control system 1100 may be embodied as any type of communication circuit, device, or collection thereof, capable of communicating with the electronic lockout system 1120. To do so, the communication circuit 1108 may utilize any suitable communication protocol including, but not limited to, Ethernet, Wi-Fi (e.g., communications based on the Institute of Electrical and Electronics Engineers (IEEE) 802.11 family), a proprietary protocol, and/or other communication protocols.

As discussed above, the electronic lockout system 1120 includes the sensor controller 1130 and the NFC sensor circuit 1140. The sensor controller 1130 may be embodied as any type of controller, circuit, or electronic device capable of generating and providing an excitation signal to the primary NFC coil 1150 to generate the magnetic field and subsequently measuring or otherwise determining the present resonant frequency of the NFC sensor circuit 1140. For example, the sensor controller 1130 may be embodied as an integrated circuit and/or including discrete digital and/or analog devices and/or circuit components. Illustratively, the sensor controller 1130 includes an NFC control circuit 1132, which is configured to control operation of the NFC sensor circuit 1140. For example, in addition to sensing whether the sled 700 is in the home position, the NFC control circuit 1132 may utilize the primary NFC coil 1150 to receive data from an NFC responder circuit 1180 located on the staple cartridge via the secondary NFC coil 1170 as discussed in more detail below. In this way, the primary NFC coil 1150 is “multi-modal.”

In the illustrative embodiment of FIG. 11, the sled 700 is embodied as a sled configured to interact with the secondary magnetic field generated between the secondary NFC coil 1170 (and, in some embodiments, with the primary magnetic field generated by the primary NFC coil 1150) when the sled 700 is located in its home position. Illustratively, the sled 700 is embedded as a metallic sled, which is illustratively embodiment as a “fully-embodied” metallic sled formed completely from a metallic material or include metallic features. However, in other embodiments, the sled 700 may be formed from other materials and/or have only partial metallic features.

In some embodiments, as discussed above, the staple cartridge 250 may also include an NFC responder circuit 1180, which may include a data storage 1182. The NFC responder circuit 1180 is configured to be powered by the current induced in the secondary NFC coil 1170 by the primary magnetic field generated by the primary NFC coil 1150. In response to being powered, the NFC responder circuit 1180 is configured to retrieve data stored on the data storage and transmit the data to the electronic lockout system 1120 via the secondary NFC coil 1170. To do so, the NFC responder circuit 1180 modulates the induced current, which modifies the load impedance of the secondary NFC coil 1170 and which can be detected by the NFC control circuit 1132.

Figure 12:
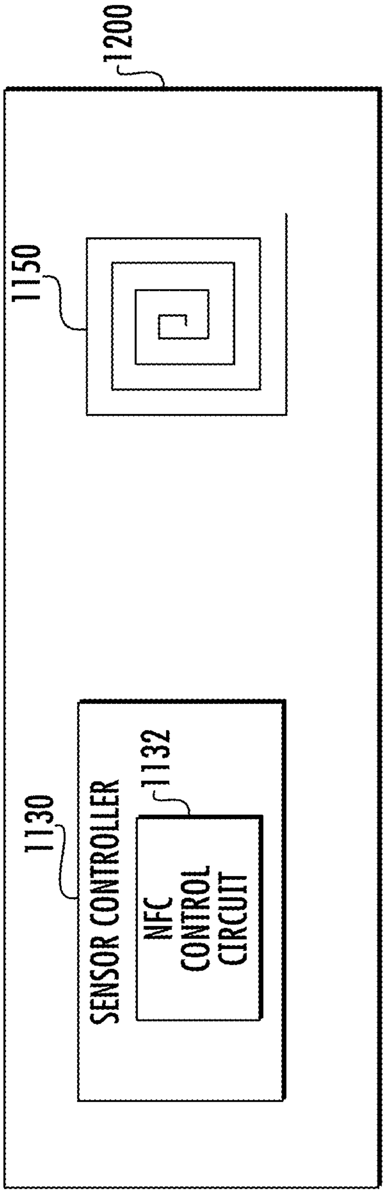
FIG. 12 is a plan view of an embodiment of the electronic lockout system of FIG. 11 including a circuit board having a sensor controller and a near filed communication (NFC) sensor circuit including a primary NFC coil mounted to the circuit board.

Referring now to FIG. 12, in the illustrative embodiment, the electronic lockout system 1120 includes a circuit board 1200 having the sensor controller 1130 and the primary NFC coil 1150 mounted thereto. The circuit board 1200 may be formed from any suitable material such as a Flame Retardant 4 (FR4) material.

Figure 13:
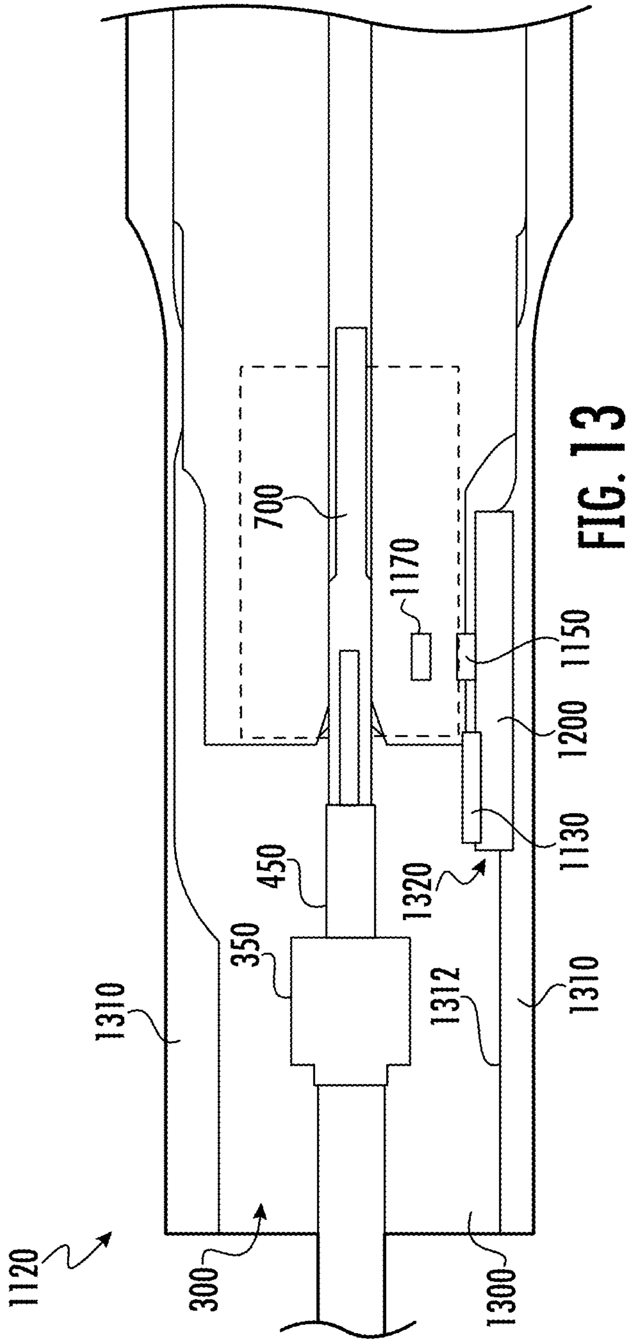
FIG. 13 is a plan view of an embodiment of a cartridge jaw of an end effector of the surgical instrument of FIG. 11 including the circuit board of the electronic lockout system of FIG. 12 received in a recess defined in a sidewall of the cartridge jaw.

As discussed above, in the illustrative embodiment, the electronic lockout system 1120 is positioned within the jaw assembly 200 such that the primary NFC coil 1150 is laterally aligned with secondary NFC coil 1170 of the staple cartridge 250 and with the sled 700 when the sled 700 is in its home position within the staple cartridge 250. To do so, the circuit board 1200 may be sized and configured to be received in a recess formed in the cartridge jaw 202. For example, as shown in FIG. 13, the illustrative cartridge jaw 202 includes a floor wall 1300 and a pair of sidewalls 1310 extending up from the floor wall 1300 to define the channel 300 of the cartridge jaw 202 configured to receive the staple cartridge 250 (see FIG. 3). In the illustrative embodiment, a recess 1320 is formed in an internal surface 1312 of the sidewall 1510, which faces the channel 300. The recess 1320 is sized and configured to receive the circuit board 1200 such that the primary NFC coil 1150 of the NFC sensor circuit 1140 is located lateral to the secondary NFC coil 1170 and the sled 700 when the sled 700 is in the home position.

Figure 14:
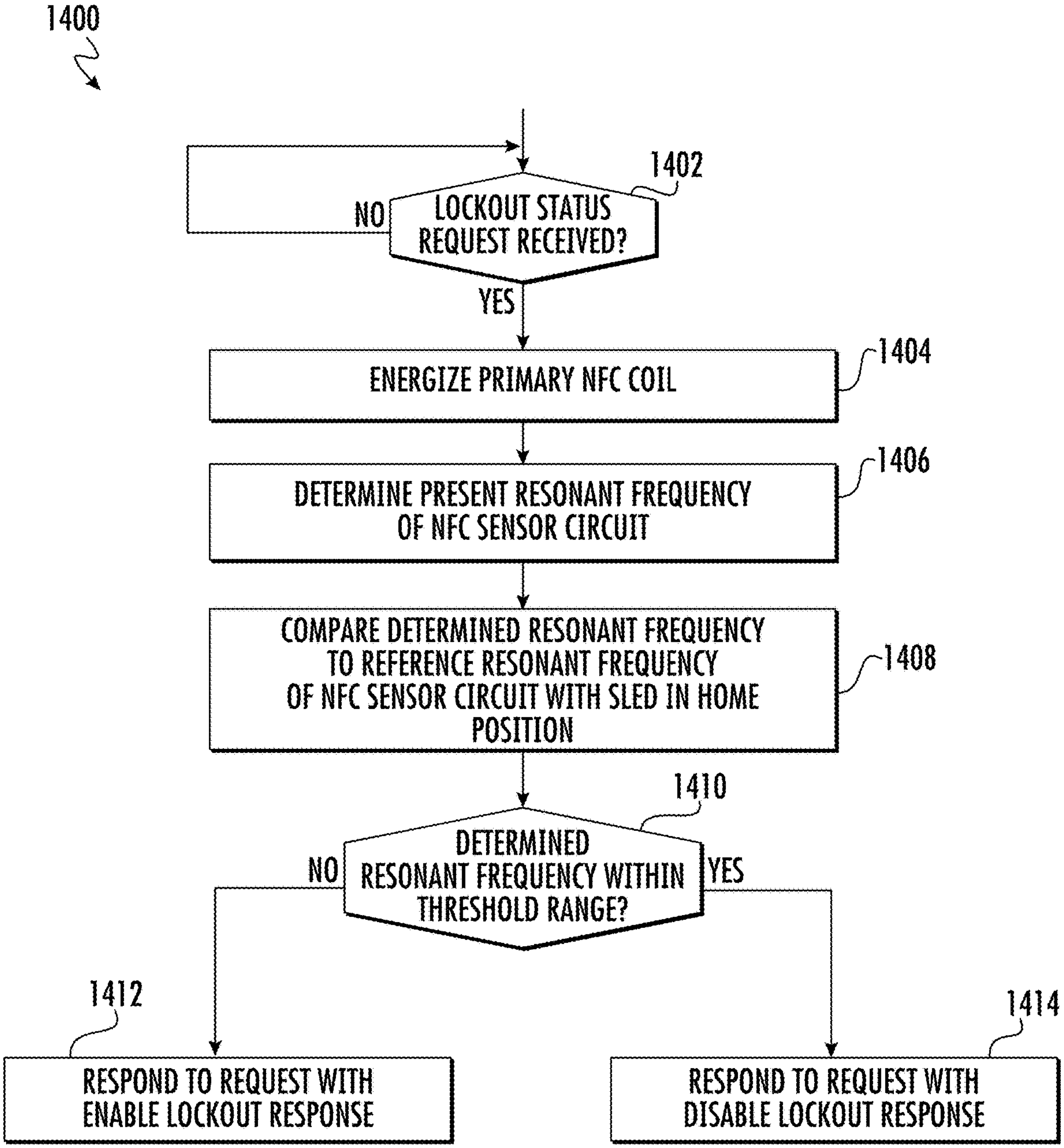
FIG. 14 is a simplified flow diagram of an embodiment of a method for enabling the electronic lockout on the surgical stapler of FIG. 11.

Referring now to FIG. 14, in use, the sensor controller 1130 of the electronic lockout system 1120 may execute a method 1400 to enable electronic lockout of the surgical stapler 100. The method 1400 begins with block 1402 in which the sensor controller 1130 determines whether a lockout status request has been received from the control system 1100. For example, prior to firing of the surgical stapler 100, the control system 1100 may be configured to issue a lockout status request to the electronic lockout system to determine whether the firing of the surgical stapler should be allowed (i.e., the electronic lockout is disabled) or prevented (i.e., the electronic lockout is enabled).

If the sensor controller 1130 determines that a lockout status request has been received from the control system 1100, the method 1400 advances to block 1404. In block 1404, the sensor controller 1130 energizes the primary NFC coil 1150 using an alternating current (AC) excitation signal. In response to the excitation signal, the primary NFC coil 1150 generates the primary magnetic field. As discussed above, the primary magnetic field induces a current in the secondary NFC coil 1170. In response to the induced current, the secondary NFC coil 1170 generates the secondary magnetic field, which is detectable by the sensor controller 1130 (i.e., the effects of the secondary magnetic field on the primary magnetic field are detectable by the sensor controller 1130).

Subsequently, in block 1406, the sensor controller 1130 determines the present resonant frequency of the NFC sensor circuit 1140. As discussed above, the primary NFC coil 1150 and the secondary NFC coil 1170 are tuned to a resonant frequency that accounts for the impact of the metallic sled 700 on the secondary magnetic field generated by the secondary NFC coil 1170 when the metallic sled 700 is in the home position. As such, when the metallic sled 700 is moved from the home position, the secondary magnetic field generated by the secondary NFC coil 1170 is altered causing the primary and secondary NFC coils 1150, 1170 to detune from the reference resonant frequency.

In block 1408, the sensor controller 1130 compares the determined resonant frequency to the reference or tuned resonant frequency of the NFC sensor circuit 1140. Subsequently, in block 1410, the sensor controller 1130 determines whether the present resonant frequency of the NFC sensor circuit 1140 is within a threshold range (i.e. a tolerance range) of the reference resonant frequency of the NFC sensor circuit 1140. Again, as discussed above, the removal of the sled 700 from the home position alters the tuned, reference resonant frequency of the NFC sensor circuit 1140. As such, if the sensor controller 1130 determines that the present resonant frequency is not within the threshold range of the tuned resonant frequency, the sensor controller 1130 determines that the sled 700 is not at the home position because the resonant frequency has changed from the reference resonant frequency. In such cases, the method 1400 advances to block 1412 in which sensor controller 1130 responds to the lockout status request with an indication to enable lockout of the surgical stapler 100. In response, the control system 1110 is configured to inhibit or prevent the firing of the surgical stapler 100.

Referring back to block 1410, if, however, the sensor controller 1130 determines that the present resonant frequency is within the threshold range of the tuned resonant frequency, the sensor controller 1130 determines that the sled 700 is at the home position because the resonant frequency has not changed from the tuned resonant frequency. As such, the method 1400 advances to block 1414 in which the sensor controller 1130 responds to the lockout status request with an indication to disable lockout of the surgical stapler 100. In response, the control system 1110 is configured to allow the firing of the surgical stapler 100.

Figure 15:
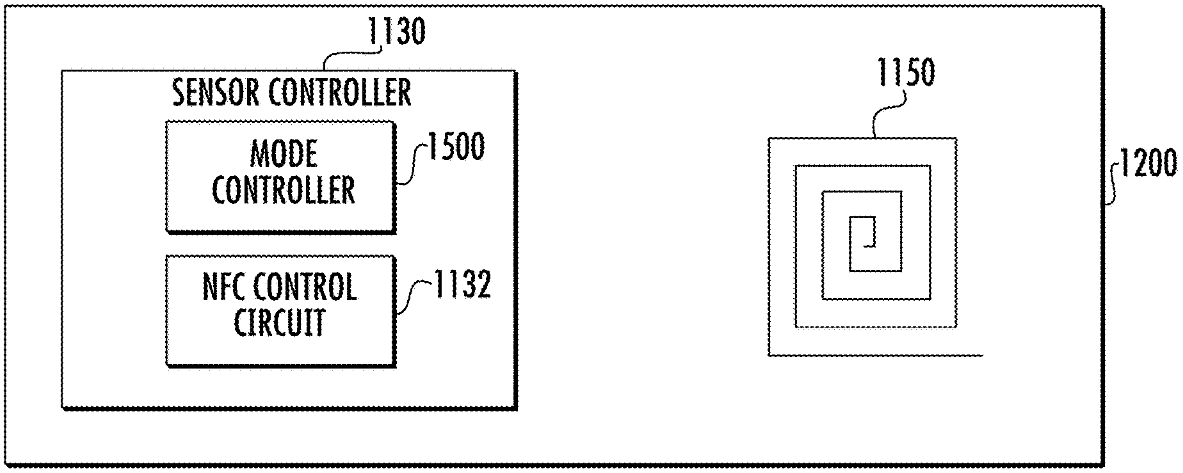
FIG. 15 is a plan view of another embodiment of the electronic lockout system of FIG. 12 in which the sensor controller includes a mode controller for configuring an NFC control circuit between an inductance sensing circuit and an NFC reader circuit.

Referring now to FIGS. 15-17B, in some embodiments, the primary NFC coil 1150 may be "multi-modal" and used as an inductance sensing coil in one mode and as a primary NFC coil for data retrieval in another mode. In such embodiments, as shown in FIG. 15, the sensor controller 1130 includes a mode controller 1500 configured to control a mode of the NFC control circuit 1132. To do so, as discussed in more detail below in regard to FIG. 16, the mode controller 1500 is configured to control or modify the circuit configuration of the NFC control circuit 1132 between an inductance sensing circuit and an NFC reader circuit. When the NFC control circuit 1132 is configured as the inductance sensing circuit, the primary NFC coil 1150 forms an inductive sensing coil of the inductance sensing circuit. Conversely, when the NFC control circuit 1132 is configured as the NFC reader circuit, the primary NFC coil 1150 forms a typical primary NFC coil of the NFC reader circuit.

Figure 16:
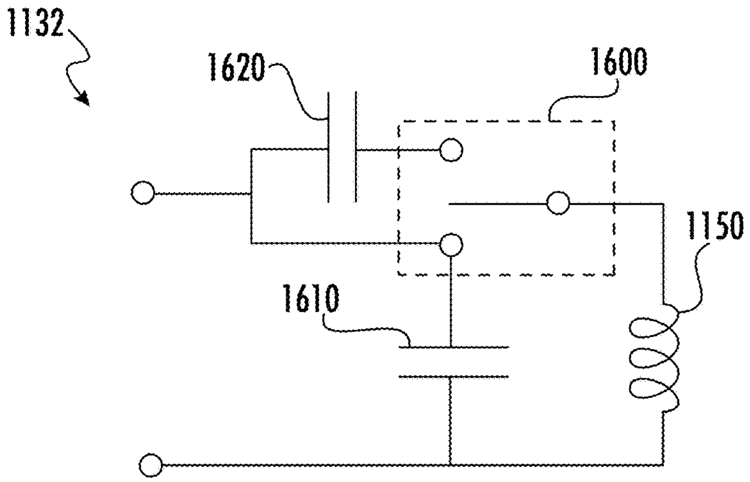
FIG. 16 is a simplified circuit diagram of one embodiment of the NFC control circuit of FIG. 15.

Referring now to FIG. 16, an illustrative embodiment of the NFC control circuit 1132 includes an electronic switch 1600, a first capacitor 1610, a second capacitor 1620, and the primary NFC coil 1150. In use, the mode controller 1500 is configured to control or activate the electronic switch 1600 to convert the NFC control circuit 1132 to the inductive sensing circuit or the NFC read circuit. For example, if an inductive sensing mode is desired, the mode controller 1500 controls the electronic switch 1600 to connect the first capacitor 1610 in parallel with the primary NFC coil 1150. In this configuration, the first capacitor 1610 and the primary NFC coil 1150 form a tank circuit. Alternatively, if an NFC reading mode is desired, the mode controller 1500 controls the electronic switch 1600 to connect the second capacitor 1620 in series with the primary NFC coil 1150. The particular capacitance values of the first and second capacitors 1610, 1620 may depend on the particular implementation, the desired reference resonant frequency of the NFC reader circuit, the inductance value of the primary NFC coil 1150, and/or other criteria.

Figure 17A:
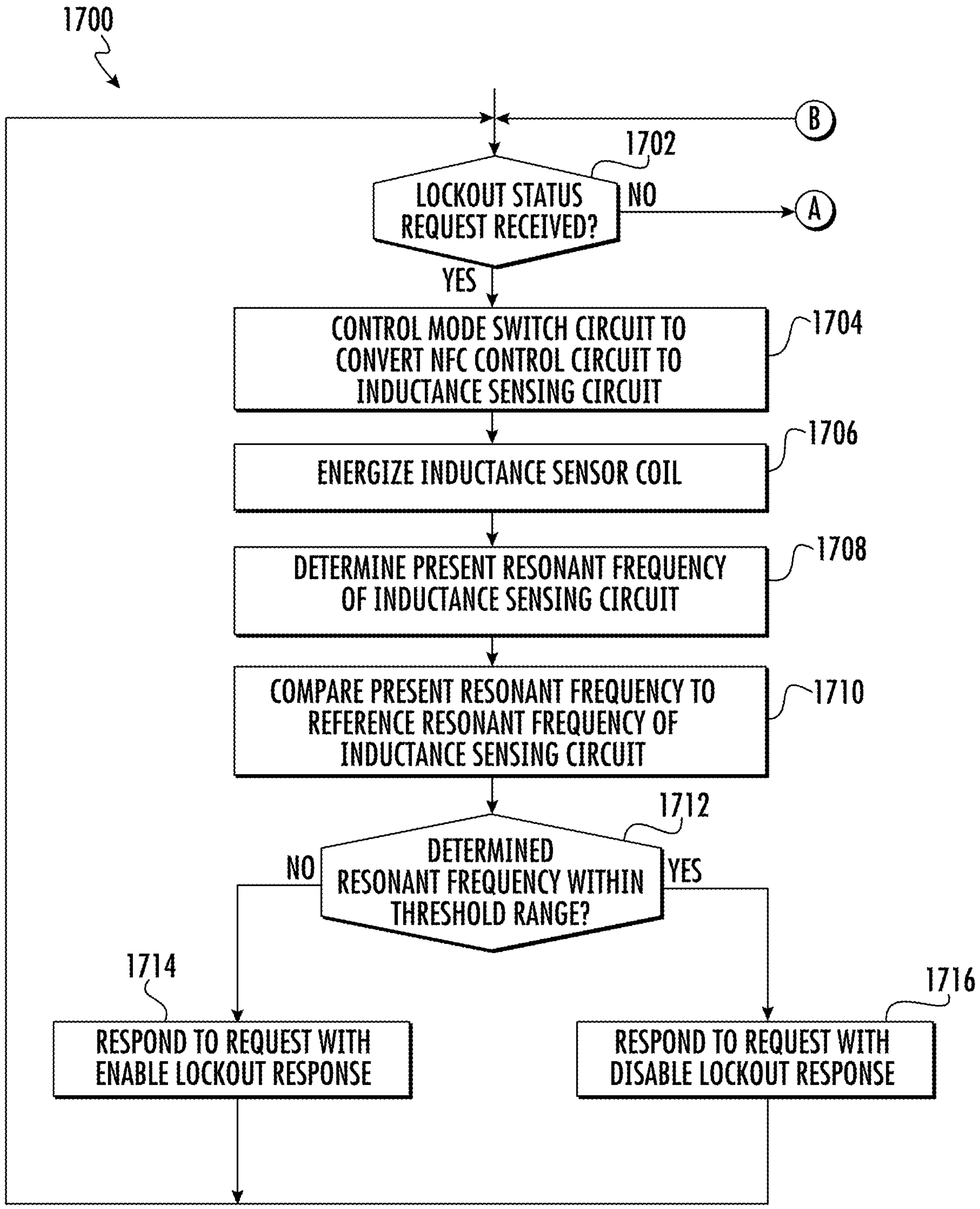
FIGS. 17A and 17B are a simplified flow diagram of another embodiment of a method for enabling the electronic lockout on the surgical stapler of FIG. 11 using the electronic lockout system of FIG. 15.
Figure 17B:
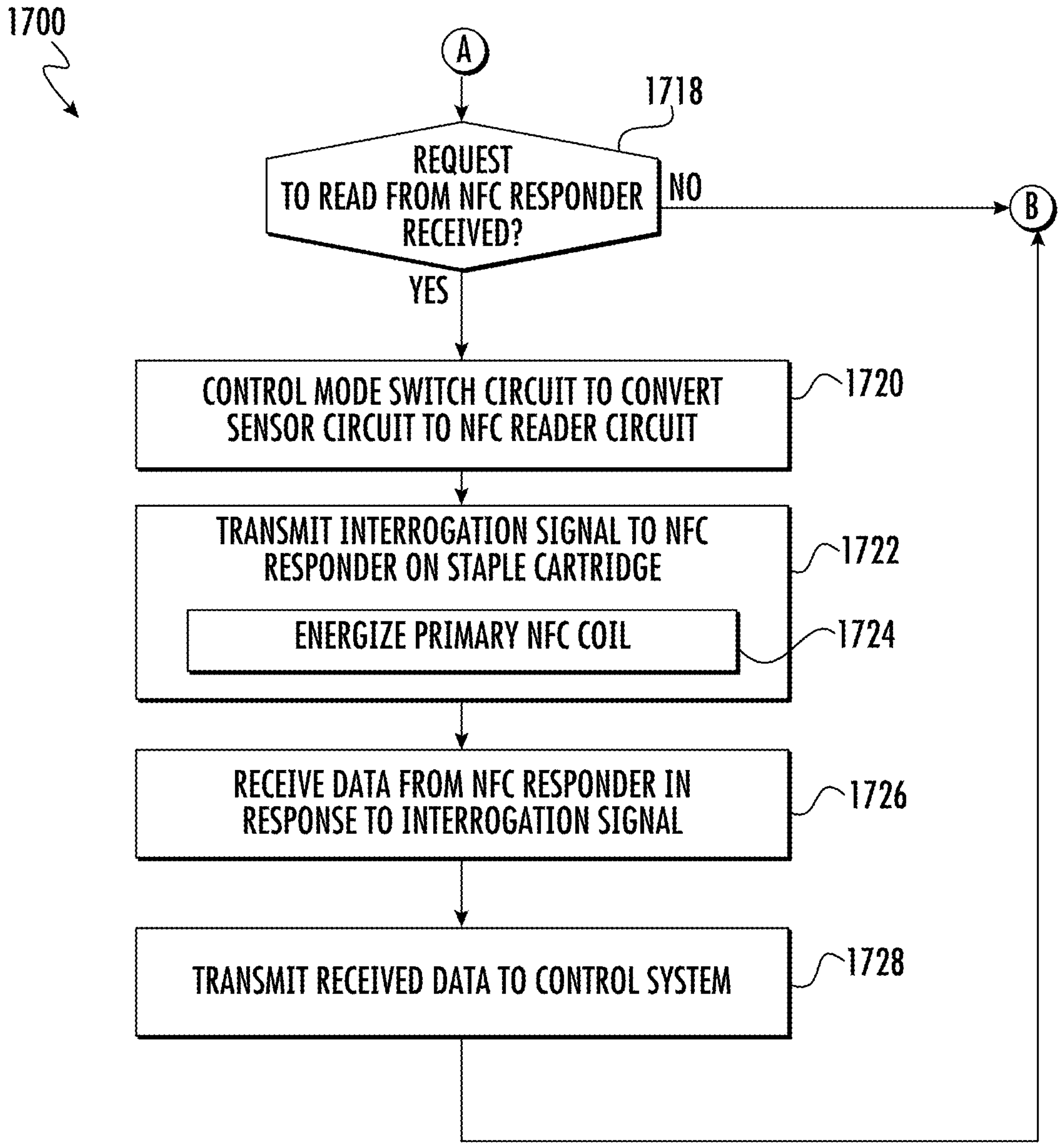

Referring now to FIGS. 17A-17B, in use, the sensor controller 1130 of FIG. 15 may execute a method 1700 to enable electronic lockout of the surgical stapler 100 and/or retrieve data from the NFC responder circuit 1180 of the staple cartridge 250. The method 1700 begins with block 1702 in which the sensor controller 1130 determines whether a lockout status request has been received from the control system 1100. As discussed previously, prior to firing of the surgical stapler 100, the control system 1100 may be configured to issue a lockout status request to the electronic lockout system to determine whether the firing of the surgical stapler should be allowed (i.e., the electronic lockout is disabled) or prevented (i.e., the electronic lockout is enabled).

If the sensor controller 1130 determines that a lockout status request has been received from the control system 1100, the method 1700 advances to block 1704. In block 1704, the mode controller 1500 of the sensor controller 1130 controls the electronic switch 1600 of the NFC control circuit 1132 to convert the NFC control circuit 1132 to the inductance sensing circuit. As discussed above, when the NFC control circuit 1132 is configured as the inductance sensing circuit, the primary NFC coil 1150 forms an inductance sensor coil of the inductance sensing circuit. as discussed above.

Subsequently, in block 1706, the sensor controller 1130 energizes the inductance sensor coil (i.e., the primary NFC coil 1150) using an alternating current (AC) excitation signal. In response to the excitation signal, the inductance sensor coil (i.e., the primary NFC coil 1150) generates a local magnetic field.

In block 1708, the sensor controller 1130 determines the present resonant frequency of the inductance sensing circuit. It should be appreciated that when the metallic sled 700 is in the home position, the magnetic field generated by the inductance sensor coil (i.e., the primary NFC coil 1150) induces eddy currents to form in the metallic sled 700, which causes the metallic sled 700 to generate its own magnetic field that interacts with the generated magnetic field of the inductance sensor coil (i.e., the primary NFC coil 1150) and changes the present resonant frequency of the inductance sensing circuit.

In block 1710, the sensor controller 1130 compares the determined resonant frequency to the reference resonant frequency of the inductance sensing circuit. In the illustrative embodiment, the reference resonant frequency is determined assuming the sled 700 is in its home position and interacting with the magnetic field generated by the inductance sensor coil (i.e., the primary NFC coil 1150). The specific resonant frequency to which the inductance sensing circuit is tuned, with the sled 700 in the home position, may vary based on the particular implementation, the composition of the sled 700, and/or other criteria.

Subsequently, in block 1712, the sensor controller 1130 determines whether the present resonant frequency of the inductance sensing circuit is within a threshold range (i.e. a tolerance range) of the reference resonant frequency of the inductance sensing circuit. If the sensor controller 1130 determines that the present resonant frequency is not within the threshold range of the reference resonant frequency, the sensor controller 1130 determines that the sled 700 is not at the home position because the resonant frequency changed from the reference resonant frequency of the inductance sensing circuit. In such cases, the method 1700 advances to block 1714 in which sensor controller 1130 responds to the lockout status request with an indication to enable lockout of the surgical stapler 100. In response, the control system 1110 is configured to inhibit or prevent the firing of the surgical stapler 100.

Referring back to block 1712, if, however, the sensor controller 1130 determines that the present resonant frequency is within the threshold range of the reference resonant frequency, the sensor controller 1130 determines that the sled 700 is at the home position because the resonant frequency has not changed from the reference resonant frequency. As such, the method 1700 advances to block 1716 in which the sensor controller 1130 responds to the lockout status request with an indication to disable lockout of the surgical stapler 100. In response, the control system 1110 is configured to allow the firing of the surgical stapler 100.

Referring now back to block 1702, if the sensor controller 1130 determines that a lockout status request has not been received from the control system 1100, the method 1700 advances to block 1718 of FIG. 17B. In block 1718, the sensor controller 1130 determines whether a request to read from the NFC responder circuit 1180 of the staple cartridge 250 has been received. If so, the method 1700 advances to block 1720 in which the mode controller 1500 of the sensor controller 1130 controls the electronic switch 1600 of the NFC control circuit 1132 to convert the NFC control circuit 1132 to the NFC reader circuit. As discussed above, when the NFC control circuit 1132 is configured as the NFC reader circuit, the primary NFC coil 1150 forms an NFC coil of the NFC reader circuit.

Subsequently, in block 1722, the sensor controller 1130 transmits an interrogation signal to the NFC responder circuit 1180 via the secondary NFC coil 1170. To do so, in block 1724, the sensor controller 1130 energizes the primary NFC coil 1150 using an alternating current (AC) excitation signal. In response to the excitation signal, the primary NFC coil 1150 generates a primary magnetic field. Again, as discussed above, the primary magnetic field induces a current in the secondary NFC coil 1170, which provides power to the NFC responder circuit 1180. When powered, the NFC responder circuit 1180 is configured to retrieve data form the data storage 1182 and transmit the data to the sensor controller 1130 via modulating the current induced in the secondary NFC coil 1170. The modulated current alters the secondary magnetic field generated by the secondary NFC coil 1170, which is detectable as data information by the NFC reader circuit.

In block 1726, the sensor controller 1130 receives the data from the NFC responder circuit 1180 in response to the interrogation signal. Subsequently, in block 1728, the sensor controller transmits the received data to the control system 1110. The method 1700 subsequently loops back to block 1702 of FIG. 17A in which the sensor controller 1130 again determine whether a lockout status request has been received from the control system 1110.

Referring now to FIGS. 18-20B, in some embodiments, the NFC sensor circuit 1140 may include both the primary NFC coil 1150 and an inductance sensor coil 1850. In such embodiments, mode controller 1500 is configured to selectively electrically couple the inductance sensor coil 1850 to the NFC control circuit 1132 to form the inductance sensing circuit or the primary NFC coil 1150 to the NFC control circuit 1132 to form the NFC reader circuit.

Figure 19:
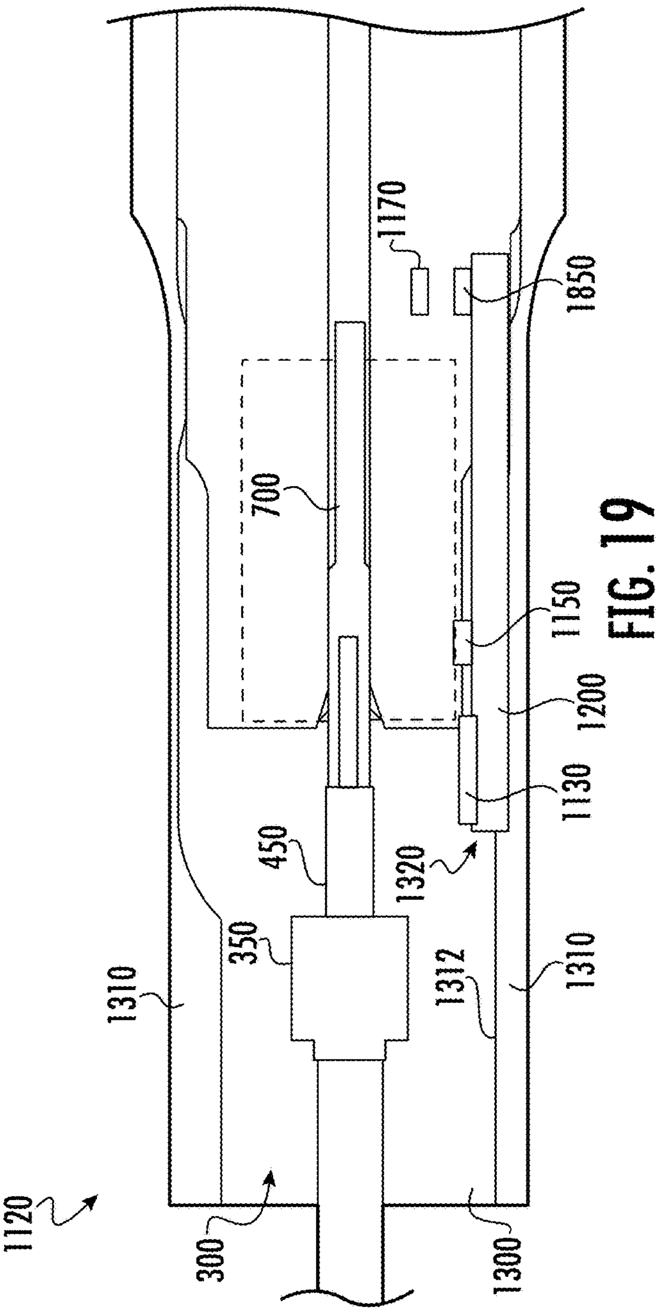
FIG. 19 is a plan view of an embodiment of the cartridge jaw of the end effector of the surgical instrument of FIG. 11 including the circuit board of the electronic lockout system of FIG. 18 received in a recess defined in a sidewall of the cartridge jaw.

In embodiments in which the NFC sensor circuit 1140 includes both the primary NFC coil 1150 and the inductance sensor coil 1850, the primary NFC coil 1150 may be longitudinally spaced from the sled 700 to improve the mutual inductance with the secondary NFC coil 1170. For example, as shown in FIG. 19, the circuit board 1200 may be received in the recess 1320 and positioned within the jaw assembly 200 such that the inductance sensor coil 1850 is laterally aligned with the sled 700 while the primary NFC coil 1150 and the secondary NFC coil 1170 are spaced away from the sled 700.

Figure 18:
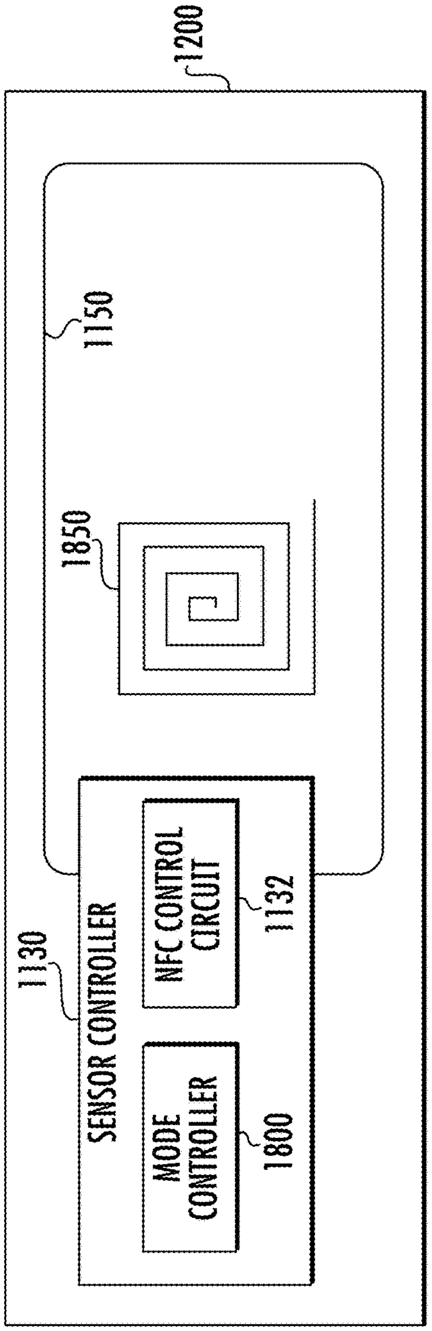
FIG. 18 is a plan view of another embodiment of the electronic lockout system of FIG. 15 in which the NFC sensor circuit includes a primary NFC coil and an inductance sensor coil.
Figure 20A:
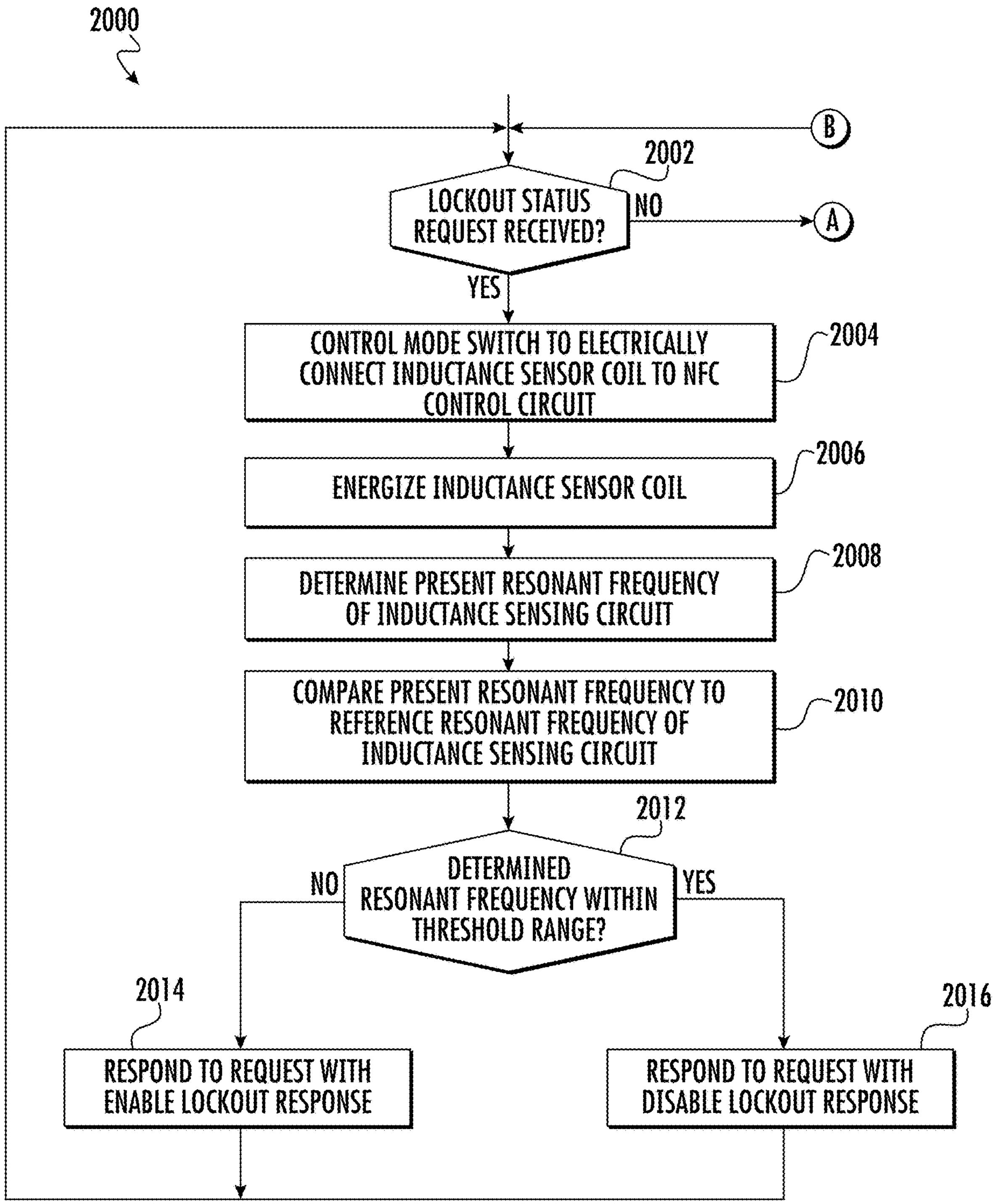
FIGS. 20A and 20B are a simplified flow diagram of yet another embodiment of a method for enabling the electronic lockout on the surgical stapler of FIG. 11 using the electronic lockout system of FIG. 18.
Figure 20B:
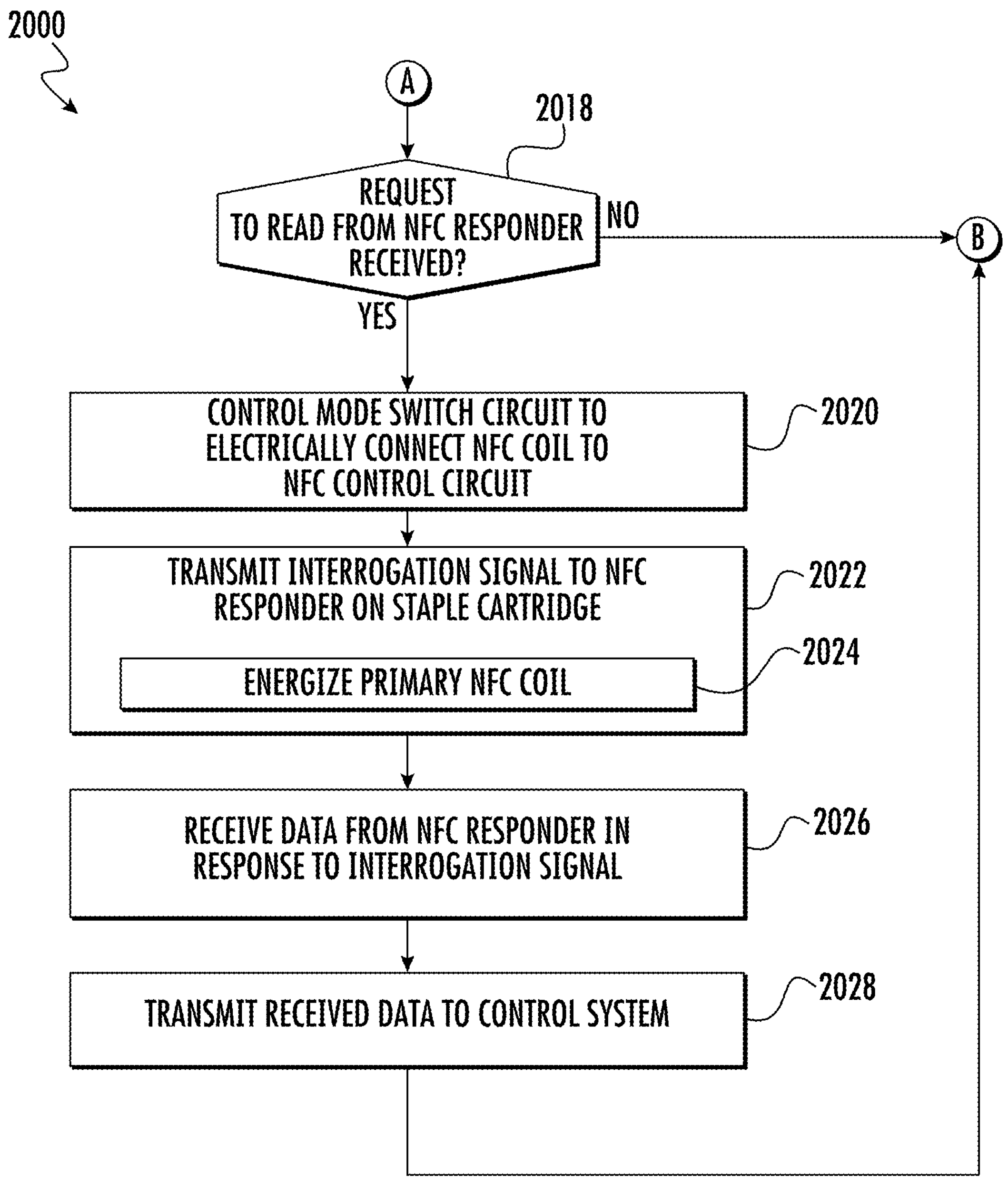

Referring now to FIGS. 20A-20B, in use, the sensor controller 1130 of FIG. 18 may execute a method 2000 to enable electronic lockout of the surgical stapler 100 and/or retrieve data from the NFC responder circuit 1180 of the staple cartridge 250. The method 2000 begins with block 2002 in which the sensor controller 1130 determines whether a lockout status request has been received from the control system 1100. As discussed previously, prior to firing of the surgical stapler 100, the control system 1100 may be configured to issue a lockout status request to the electronic lockout system to determine whether the firing of the surgical stapler should be allowed (i.e., the electronic lockout is disabled) or prevented (i.e., the electronic lockout is enabled).

If the sensor controller 1130 determines that a lockout status request has been received from the control system 1100, the method 2000 advances to block 2004. In block 2004, the mode controller 1500 of the sensor controller 1130 electrically connects the inductance sensor coil 1850 to the NFC control circuit 1132 (and disconnects the primary NFC coil 1150) to convert the NFC control circuit 1132 to the inductance sensing circuit. Subsequently, in block 2006, the sensor controller 1130 energizes the inductance sensor coil 1850 using an alternating current (AC) excitation signal. In response to the excitation signal, the inductance sensor coil 1850 generates a local magnetic field.

In block 2008, the sensor controller 1130 determines the present resonant frequency of the inductance sensing circuit. Again, it should be appreciated that when the metallic sled 700 is in the home position, the magnetic field generated by the inductance sensor coil (i.e., the primary NFC coil 1150) induces eddy currents to form in the metallic sled 700, which causes the metallic sled 700 to generate its own magnetic field that interacts with the generated magnetic field of the inductance sensor coil (i.e., the primary NFC coil 1150) and changes the present resonant frequency of the inductance sensing circuit.

In block 2010, the sensor controller 1130 compares the determined resonant frequency to the reference resonant frequency of the inductance sensing circuit. Again, in the illustrative embodiment, the reference resonant frequency is determined assuming the sled 700 is in its home position and interacting with the magnetic field generated by the inductance sensor coil (i.e., the primary NFC coil 1150). The specific resonant frequency to which the inductance sensing circuit is tuned, with the sled 700 in the home position, may vary based on the particular implementation, the composition of the sled 700, and/or other criteria.

Subsequently, in block 2012, the sensor controller 1130 determines whether the present resonant frequency of the inductance sensing circuit is within a threshold range (i.e. a tolerance range) of the reference resonant frequency of the inductance sensing circuit. If the sensor controller 1130 determines that the present resonant frequency is not within the threshold range of the reference resonant frequency, the sensor controller 1130 determines that the sled 700 is not at the home position because the resonant frequency changed from the reference resonant frequency of the inductance sensing circuit. In such cases, the method 2000 advances to block 2014 in which sensor controller 1130 responds to the lockout status request with an indication to enable lockout of the surgical stapler 100. In response, the control system 1110 is configured to inhibit or prevent the firing of the surgical stapler 100.

Referring back to block 2012, if, however, the sensor controller 1130 determines that the present resonant frequency is within the threshold range of the reference resonant frequency, the sensor controller 1130 determines that the sled 700 is at the home position because the resonant frequency has not changed from the reference resonant frequency. As such, the method 2000 advances to block 2016 in which the sensor controller 1130 responds to the lockout status request with an indication to disable lockout of the surgical stapler 100. In response, the control system 1110 is configured to allow the firing of the surgical stapler 100.

Referring now back to block 2002, if the sensor controller 1130 determines that a lockout status request has not been received from the control system 1100, the method 2000 advances to block 2018 of FIG. 20B. In block 2018, the sensor controller 1130 determines whether a request to read from the NFC responder circuit 1180 of the staple cartridge 250 has been received. If so, the method 2000 advances to block 2018 in which the mode controller 1500 of the sensor controller 1130 electrically connects the primary NFC coil 1150 to the NFC control circuit 1132 (and disconnects the inductance sensor coil 1850) to convert the NFC control circuit 1132 to the NFC reader circuit.

Subsequently, in block 2022, the sensor controller 1130 transmits an interrogation signal to the NFC responder circuit 1180 via the secondary NFC coil 1170. To do so, in block 2024, the sensor controller 1130 energizes the primary NFC coil 1150 using an alternating current (AC) excitation signal. In response to the excitation signal, the primary NFC coil 1150 generates a primary magnetic field. Again, as discussed above, the primary magnetic field induces a current in the secondary NFC coil 1170, which provides power to the NFC responder circuit 1180. When powered, the NFC responder circuit 1180 is configured to retrieve data form the data storage 1182 and transmit the data to the sensor controller 1130 via modulating the current induced in the secondary NFC coil 1170. The modulated current alters the secondary magnetic field generated by the secondary NFC coil 1170, which is detectable as data information by the NFC reader circuit.

In block 2026, the sensor controller 1130 receives the data from the NFC responder circuit 1180 in response to the interrogation signal. Subsequently, in block 2028, the sensor controller transmits the received data to the control system 1110. The method 2000 subsequently loops back to block 2002 of FIG. 20A in which the sensor controller 1130 again determine whether a lockout status request has been received from the control system 1110.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

EXAMPLES

Example 1 includes a surgical stapler having an end effector, a sensor controller, and an NFC sensor circuit including a primary NFC coil. The end effector is configured to receive the staple cartridge and includes a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller is configured to energize the primary NFC coil to generate a primary magnetic field to induce a current in the secondary NFC coil, determine a first resonant frequency of the NFC sensor circuit based on the primary magnetic field and a secondary magnetic field generated by the secondary NFC coil, compare the first resonant frequency of the NFC sensor circuit to an expected resonant frequency of the NFC sensor circuit when the metallic sled is in the home position and interacting with the magnetic field generated by the primary NFC coil, and determine, based on the comparison of the first resonant frequency and the expected resonant frequency, whether to enable lockout of the surgical stapler to prevent firing of the surgical stapler.

Example 2 includes the subject matter of Example 1, and wherein the end effector includes a jaw assembly having a cartridge jaw and an anvil jaw opposite the cartridge jaw. The cartridge jaw includes a floor wall and a pair of opposing sidewalls extending up from the floor wall to define a channel configured to receive the staple cartridge. A first sidewall of the pair of opposing sidewalls includes a recess defined on an internal surface facing the channel. The surgical stapler may include a circuit board, and the sensor controller and the NFC sensor circuit are mounted on the circuit board. The circuit board is located within the recess of the first sidewall such that the NFC primary coil of the NFC sensor circuit is laterally adjacent to the metallic sled when the metallic sled is in the home position.

Example 3 includes the subject matter of any of Examples 1 or 2, and wherein the first resonant frequency of the NFC sensor circuit is dependent on whether the metallic sled is located in the home position and interacting with the magnetic field generated by the secondary NFC sensor coil.

Example 4 includes the subject matter of any of Examples 1-3, and wherein the primary NFC coil and the secondary NFC coil are tuned to the expected resonant frequency with the metallic sled in the home position.

Example 5 includes the subject matter of any of Examples 1-4, and wherein the sensor controller includes an NFC reader circuit configured to energize the primary NFC coil to generate a magnetic field to induce a current in the secondary NFC coil of the staple cartridge and receive, in response to the induced current, data from a responder circuit of the staple cartridge transferred via the secondary NFC coil.

Example 6 includes the subject matter of any of Examples 1-5, and wherein the sensor controller is further configured to respond to the lockout status request with an indication of whether the lockout of the surgical stapler is enabled or disabled based on the first resonant frequency of the inductance sensor circuit.

Example 7 includes a surgical stapler having an end effector, a sensor controller, and an NFC sensor circuit located in the end effector and including a primary NFC coil. The end effector is configured to receive the staple cartridge. The staple cartridge includes a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller includes a mode controller and an NFC control circuit. The mode controller is configured to selectively configure the NFC control circuit between an inductance sensing circuit and an NFC reader circuit. The primary NFC coil forms an inductance sensor coil of the inductance sensing circuit while the NFC control circuit is configured as the inductance sensing circuit. The sensor controller is configured to use the inductance sensing circuit to determine whether the sled is in the home position and use the NFC reader circuit to read data from the staple cartridge via the secondary NFC coil.

Example 8 includes the subject matter of Example 7, and wherein the sensor controller is configured to determine a mode for the NFC control circuit between an inductance sensing mode and an NFC reading mode. The sensor controller is further configured to, in response to a determination that the mode for the NFC control circuit is the inductance sensing mode, control the mode controller to configure the NFC control circuit as the inductance sensing circuit; energize, using the inductance sensing circuit, the inductance sensor coil to generate a magnetic field; determine a first resonant frequency of the inductance sensing circuit based on the magnetic field; compare the first resonant frequency of the inductance sensing circuit to an expected resonant frequency of the inductance sensing circuit; and determine, based on the comparison of the first resonant frequency and the expected resonant frequency, whether to enable lockout of the surgical stapler to prevent firing of the surgical stapler.

Example 9 includes the subject matter of any of Examples 7 or 8, and wherein the inductance sensor circuit comprises a tank circuit having a capacitor and the inductance sensor coil.

Example 10 includes the subject matter of any of Examples 7-9, and wherein the first resonant frequency of the NFC sensor circuit is dependent on whether the metallic sled is located in the home position and interacting with the magnetic field generated by the inductance sensing circuit.

Example 11 includes the subject matter of any of Examples 7-10, and wherein the primary NFC coil and the secondary NFC coil are tuned to the expected resonant frequency with the metallic sled in the home position.

Example 12 includes the subject matter of any of Examples 7-11, and wherein the sensor controller is further configured to respond to the lockout status request with an indication of whether the lockout of the surgical stapler is enabled or disabled based on the first resonant frequency of the inductance sensing circuit.

Example 13 includes the subject matter of any of Examples 7-12, and wherein the sensor controller is configured to determine a mode for the NFC control circuit between an inductance sensing mode and an NFC reading mode. The sensor controller is further configured to, in response to a determination that the mode for the NFC control circuit is the NFC reading mode, control the mode controller to configure the NFC control circuit as the NFC reader circuit; energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil.

Example 14 includes the subject matter of any of Examples 7-13, and wherein the mode controller is configured to control an electronic switch to selectively couple either (i) a first capacitor in series with the primary NFC coil to form the NFC reader circuit or (ii) a second capacitor in parallel with the primary NFC coil to form the inductance sensing circuit.

Example 15 includes a surgical stapler having an end effector, a sensor controller, and an NFC sensor circuit including a primary NFC coil and an inductance sensor coil. The end effector is configured to receive the staple cartridge. The staple cartridge includes a plurality of surgical staples, a metallic sled movable, in response to a firing of the surgical stapler, from a home position to a spent position within the staple cartridge to eject the surgical staples from the staple cartridge, and a secondary near field communication (NFC) coil. The sensor controller includes a mode controller and an NFC control circuit. The mode controller is configured to selectively configure the NFC control circuit between (i) an inductance sensing circuit by electrically coupling the inductance sensor coil to the NFC control circuit and (ii) an NFC reader circuit by electrically coupling the primary NFC coil to the NFC control circuit. The sensor controller is configured to use the inductance sensing circuit to determine whether the sled is in the home position and use the NFC reader circuit to read data from the staple cartridge via the secondary NFC coil.

Example 16 includes the subject matter of Example 15, and wherein the sensor controller is configured to determine a mode for the NFC control circuit between an inductance sensing mode and an NFC reading mode. The sensor controller is further configured to, in response to a determination that the mode for the NFC control circuit is the inductance sensing mode, control the mode controller to electrically couple the inductance sensor coil to the NFC control circuit to form the inductance sensing circuit; energize, using the inductance sensing circuit, the inductance sensor coil to generate a magnetic field; determine a first resonant frequency of the inductance sensing circuit based on the magnetic field; compare the first resonant frequency of the inductance sensing circuit to an expected resonant frequency of the inductance sensing circuit; and determine, based on the comparison of the first resonant frequency and the expected resonant frequency, whether to enable lockout of the surgical stapler to prevent firing of the surgical stapler.

Example 17 includes the subject matter of any of Examples 15 or 16, and wherein the first resonant frequency of the inductance sensing circuit is dependent on whether the metallic sled is located in the home position and interacting with the magnetic field generated by the inductance sensing coil.

Example 18 includes the subject matter of any of Examples 15-17, and wherein the inductance sensing coil is tuned to the expected resonant frequency with the metallic sled in the home position.

Example 19 includes the subject matter of any of Examples 15-18, and wherein the sensor controller is further configured to respond to the lockout status request with an indication of whether the lockout of the surgical stapler is enabled or disabled based on the first resonant frequency of the inductance sensing circuit.

Example 20 includes the subject matter of any of Examples 15-19 wherein the sensor controller is configured to determine a mode for the NFC control circuit between an inductance sensing mode and an NFC reading mode. The sensor controller is further configured to, in response to a determination that the mode for the NFC control circuit is the NFC reading mode, control the mode controller to electrically couple the primary NFC coil to the NFC control circuit to form the NFC reader circuit; energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil.

The invention claimed is:

1. A surgical stapler comprising:

an end effector configured to receive the staple cartridge, wherein the staple cartridge includes a plurality of surgical staples, a metallic sled movable, in response to a firing of the surgical stapler, from a home position to a spent position within the staple cartridge to eject the surgical staples from the staple cartridge, and a secondary near field communication (NFC) coil;

a sensor controller; and an NFC sensor circuit including a primary NFC coil, wherein the sensor controller is configured to:

energize the primary NFC coil to generate a primary magnetic field to induce a current in the secondary NFC coil, determine a first resonant frequency of the NFC sensor circuit based on the primary magnetic field and a secondary magnetic field generated by the secondary NFC coil, compare the first resonant frequency of the NFC sensor circuit to an expected resonant frequency of the NFC sensor circuit when the metallic sled is in the home position and interacting with the magnetic field generated by the primary NFC coil, and determine, based on the comparison of the first resonant frequency and the expected resonant frequency, whether to enable lockout of the surgical stapler to prevent firing of the surgical stapler.

2. The surgical stapler of claim 1, wherein the end effector comprises a jaw assembly having a cartridge jaw and an anvil jaw opposite the cartridge jaw, wherein the cartridge jaw comprises a floor wall and a pair of opposing sidewalls extending up from the floor wall to define a channel configured to receive the staple cartridge, wherein a first sidewall of the pair of opposing sidewalls includes a recess defined on an internal surface facing the channel, wherein the surgical stapler further includes a circuit board, wherein the sensor controller and the NFC sensor circuit are mounted on the circuit board, and wherein the circuit board is located within the recess of the first sidewall such that the NFC primary coil of the NFC sensor circuit is laterally adjacent to the metallic sled when the metallic sled is in the home position.

3. The surgical stapler of claim 1, wherein the present resonant frequency of the NFC sensor circuit is dependent on whether the metallic sled is located in the home position and interacting with the magnetic field generated by the secondary NFC sensor coil.

4. The surgical stapler of claim 3, wherein the primary NFC coil and the secondary NFC coil are pretuned to the expected resonant frequency with the metallic sled in the home position.

5. The surgical stapler of claim 1, wherein the sensor controller includes an NFC reader circuit configured to energize the primary NFC coil to generate a magnetic field to induce a current in the secondary NFC coil of the staple cartridge and receive, in response to the induced current, data from a responder circuit of the staple cartridge transferred via the secondary NFC coil.

6. The surgical stapler of claim 1, wherein the sensor controller is further configured to respond to the lockout status request with an indication of whether the lockout of the surgical stapler is enabled or disabled based on the present resonant frequency of the inductance sensor circuit.

7. A surgical stapler comprising:

an end effector configured to receive the staple cartridge, wherein the staple cartridge includes a plurality of surgical staples, a metallic sled movable, in response to a firing of the surgical stapler, from a home position to a spent position within the staple cartridge to eject the surgical staples from the staple cartridge, and a secondary near field communication (NFC) coil; and a sensor controller; and an NFC sensor circuit located in the end effector and including a primary NFC coil, wherein the sensor controller includes a mode controller and an NFC control circuit, wherein the mode controller is configured to selectively configure the NFC control circuit between an inductance sensing circuit and an NFC reader circuit, wherein the primary NFC coil forms an inductance sensor coil of the inductance sensing circuit while the NFC control circuit is configured as the inductance sensing circuit, and wherein the sensor controller is configured to use the inductance sensing circuit to determine whether the sled is in the home position and use the NFC reader circuit to read data from the staple cartridge via the secondary NFC coil.

8. The surgical stapler of claim 7, wherein the sensor controller is configured to determine a mode for the NFC control circuit between an inductance sensing mode and an NFC reading mode, and wherein in response to a determination that the mode for the NFC control circuit is the inductance sensing mode, the sensor controller is further configured to:

control the mode controller to configure the NFC control circuit as the inductance sensing circuit;

energize, using the inductance sensing circuit, the inductance sensor coil to generate a magnetic field;

determine a present resonant frequency of the inductance sensing circuit based on the magnetic field;

compare the present resonant frequency of the inductance sensing circuit to an expected resonant frequency of the inductance sensing circuit; and determine, based on the comparison of the present resonant frequency and the expected resonant frequency, whether to enable lockout of the surgical stapler to prevent firing of the surgical stapler.

9. The surgical stapler of claim 8, wherein the inductance sensor circuit comprises a tank circuit having a capacitor and the inductance sensor coil.

10. The surgical stapler of claim 8, wherein the present resonant frequency of the NFC sensor circuit is dependent on whether the metallic sled is located in the home position and interacting with the magnetic field generated by the inductance sensing circuit.

11. The surgical stapler of claim 8, wherein the primary NFC coil and the secondary NFC coil are pretuned to the expected resonant frequency with the metallic sled in the home position.

12. The surgical stapler of claim 8, wherein the sensor controller is further configured to respond to the lockout status request with an indication of whether the lockout of the surgical stapler is enabled or disabled based on the present resonant frequency of the inductance sensing circuit.

13. The surgical stapler of claim 7, wherein the sensor controller is configured to determine a mode for the NFC control circuit between an inductance sensing mode and an NFC reading mode, and wherein in response to a determination that the mode for the NFC control circuit is the NFC reading mode, the sensor controller is further configured to:

control the mode controller to configure the NFC control circuit as the NFC reader circuit;

energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil.

14. The surgical stapler of claim 7, wherein the mode controller is configured to control an electronic switch to selectively couple either (i) a first capacitor in series with the primary NFC coil to form the NFC reader circuit or (ii) a second capacitor in parallel with the primary NFC coil to form the inductance sensing circuit.

15. A surgical stapler comprising:

an end effector configured to receive the staple cartridge, wherein the staple cartridge includes a plurality of surgical staples, a metallic sled movable, in response to a firing of the surgical stapler, from a home position to a spent position within the staple cartridge to eject the surgical staples from the staple cartridge, and a secondary near field communication (NFC) coil;

a sensor controller; and an NFC sensor circuit including located in the end effector and a primary NFC coil and an inductance sensor coil, wherein the sensor controller includes a mode controller and an NFC control circuit, wherein the mode controller is configured to selectively configure the NFC control circuit between (i) an inductance sensing circuit by electrically coupling the inductance sensor coil to the NFC control circuit and (ii) an NFC reader circuit by electrically coupling the primary NFC coil to the NFC control circuit, and wherein the sensor controller is configured to use the inductance sensing circuit to determine whether the sled is in the home position and use the NFC reader circuit to read data from the staple cartridge via the secondary NFC coil.

16. The surgical stapler of claim 15, wherein the sensor controller is configured to determine a mode for the NFC control circuit between an inductance sensing mode and an NFC reading mode, and wherein in response to a determination that the mode for the NFC control circuit is the inductance sensing mode, the sensor controller is further configured to:

control the mode controller to electrically couple the inductance sensor coil to the NFC control circuit to form the inductance sensing circuit;

energize, using the inductance sensing circuit, the inductance sensor coil to generate a magnetic field;

determine a present resonant frequency of the inductance sensing circuit based on the magnetic field;

compare the present resonant frequency of the inductance sensing circuit to an expected resonant frequency of the inductance sensing circuit; and determine, based on the comparison of the present resonant frequency and the expected resonant frequency, whether to enable lockout of the surgical stapler to prevent firing of the surgical stapler.

17. The surgical stapler of claim 16, wherein the present resonant frequency of the inductance sensing circuit is dependent on whether the metallic sled is located in the home position and interacting with the magnetic field generated by the inductance sensing coil.

18. The surgical stapler of claim 16, wherein the inductance sensing coil is pretuned to the expected resonant frequency with the metallic sled in the home position.

19. The surgical stapler of claim 16, wherein the sensor controller is further configured to respond to the lockout status request with an indication of whether the lockout of the surgical stapler is enabled or disabled based on the present resonant frequency of the inductance sensing circuit.

20. The surgical stapler of claim 15, wherein the sensor controller is configured to determine a mode for the NFC control circuit between an inductance sensing mode and an NFC reading mode, and wherein in response to a determination that the mode for the NFC control circuit is the NFC reading mode, the sensor controller is further configured to:

control the mode controller to electrically couple the primary NFC coil to the NFC control circuit to form the NFC reader circuit;

energize, using the NFC reader circuit, the primary NFC coil to generate a magnetic field to induce a current in the secondary NFC coil of the staple cartridge, and receive, in response to the induced current, data from a responder circuit of the staple cartridge transferred via the secondary NFC coil.

* * * * *